(12) United States Patent
Kidd et al.

(10) Patent No.: US 7,052,834 B1
(45) Date of Patent: May 30, 2006

(54) TUMOR SUPPRESSOR PROTEIN INVOLVED IN DEATH SIGNALING, AND DIAGNOSTICS, THERAPEUTICS, AND SCREENING BASED ON THIS PROTEIN

(75) Inventors: Vincent J. Kidd, Memphis, TN (US); Jill M. Lahti, Memphis, TN (US); Tal Teitz, Cordova, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 09/477,082

(22) Filed: Dec. 30, 1999

Related U.S. Application Data

(60) Provisional application No. 60/114,308, filed on Dec. 31, 1998.

(51) Int. Cl.
*C12Q 1/68* (2006.01)
*C07H 21/04* (2006.01)

(52) U.S. Cl. .................. 435/6; 435/4; 436/63; 436/64; 536/24.1; 536/24.3; 536/24.31; 536/24.33

(58) Field of Classification Search .................. 435/4, 435/6, 7.1, 7.721, 7.23, 91.2; 436/501, 503, 436/504, 808, 63, 64; 536/24.1, 24.3, 24.31, 536/24.33
See application file for complete search history.

(56) References Cited

U.S. PATENT DOCUMENTS 6,172,190 B1 * 1/2001 Hunter et al. ............... 530/350

FOREIGN PATENT DOCUMENTS

| WO | WO 97/03998 | 2/1997 |
|----|-------------|--------|
| WO | WO 97/35020 | 9/1997 |
| WO | WO 97/46662 | 12/1997 |
| WO | WO 98/38200 | 9/1998 |
| WO | WO 98/39435 | 9/1998 |

OTHER PUBLICATIONS

Herman et al., PNAS vol. 91, pp. 9700-9704, Oct. 1994.*
Herman et al., PNAS, vol. 93, pp. 9821-9826, Sep. 1996.*
Scaffidi, C., et al, Journal of Biol. Chem., 272(43): 26953-26958, Oct. 1997.*
Boehringer Mannheim, Biochemical Catalog, p. 95, 1997.*
Harada, K. et al. Deregulation of Caspase 8 and 10 expression in pediatric tumors and cell lines. Cancer Research, 62: 5897-5901, 2002.*
Jou et al., Current Biology, 8(18):1001-1008, 1998.
Mandruzzato et al., J. Exp. Med., 186(5):785-793, 1997.
Sakamaki et al., Eur. J. Biochem, 253:399-405, 1998.

* cited by examiner

*Primary Examiner*—Alana M. Harris
*Assistant Examiner*—Anne L. Holleran
(74) *Attorney, Agent, or Firm*—Darby & Darby

(57) ABSTRACT

The present invention relates to identification of tumor suppressor activity of a protein, caspase-8 (CASP8), and to related diagnostic and therapeutic compositions and methods. The discovery of this tumor suppressor activity provides screening targets as well, particularly screening for compounds that overcome gene inactivation that results from genomic methylation of the promoter. In particular, CASP8 is functionally inactivated in greater than 90% of all MYCN amplified neuroblastoma cell lines analyzed. Inactivation of CASP8 was observed to occur by homozygous deletion, heterozygous deletion coupled with gene silencing by methylation, and homozygous gene silencing by methylation. A PCR methylation analysis for inactivation of CASP8 is described.

13 Claims, 13 Drawing Sheets

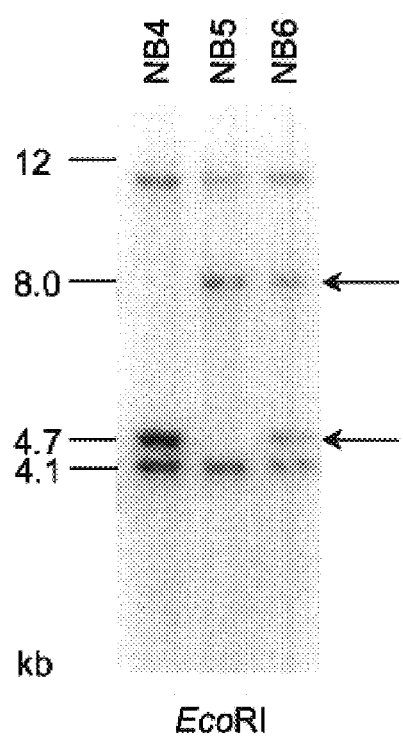
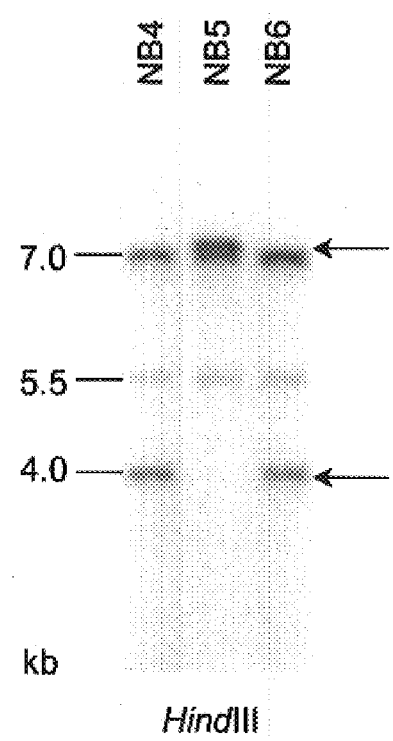

Deleted CASP8 allele

Normal CASP8 allele

Chromosome 2

Caspase 8

Caspase 10

FIG. 6A
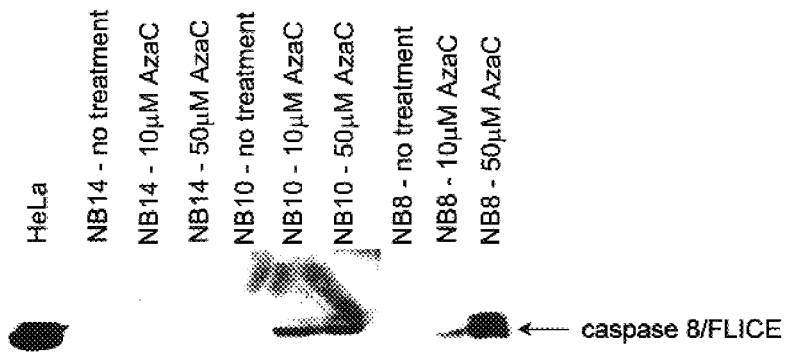
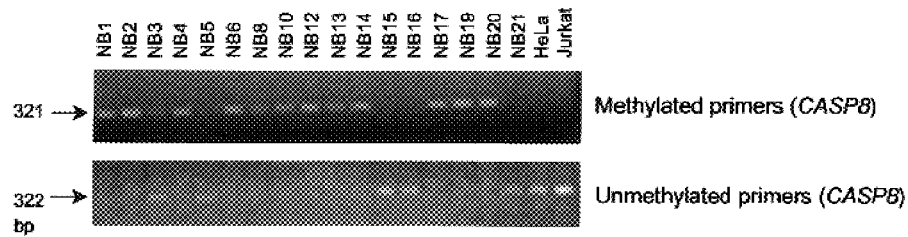
FIG. 6B

NB7/Casp8
(TNFα+CHX)

5 hrs.

Numarski

NB7/Casp8
(TNFα+CHX)

5 hrs.

DAPI

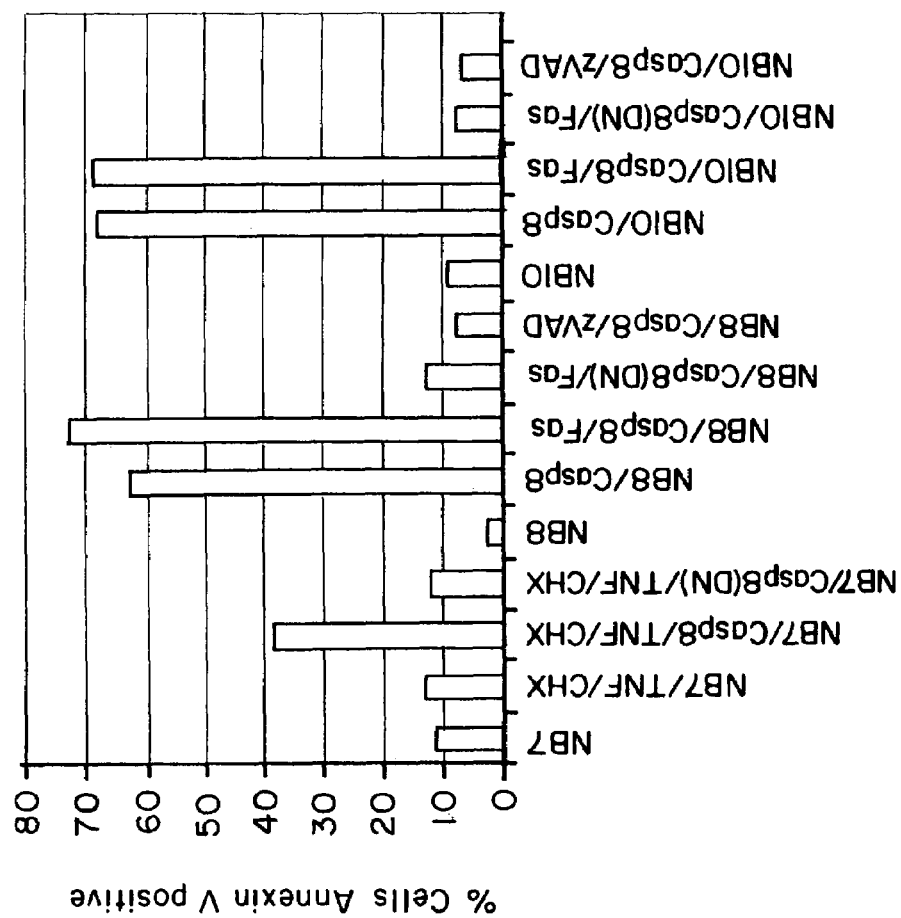

TUMOR SUPPRESSOR PROTEIN INVOLVED IN DEATH SIGNALING, AND DIAGNOSTICS, THERAPEUTICS, AND SCREENING BASED ON THIS PROTEIN

This patent application claims the priority of U.S. provisional patent application No. 60/114,308, filed Dec. 31, 1998, which is incorporated herein by reference.

The research leading to this invention was supported in part by National Institutes of Health grant no. CA 67938 and National Institutes of Health Cancer Center Core grant no. CA 21765.

FIELD OF THE INVENTION

The present invention relates to identification of tumor suppressor activity of a protein, and to related diagnostic and therapeutic compositions and methods. The discovery of this tumor suppressor activity provides screening targets as well, particularly screening for compounds that overcome gene inactivation that results from genomic methylation of the promoter.

BACKGROUND OF THE INVENTION

The cysteine proteases caspase-8 (alternatively named FLICE1/MACH1), caspase 9 (alternatively named Apaf 3/Mch6) and caspase-10 (alternatively named FLICE2/MACH 2) are related proteins that share homology with the prototypic member of the larger caspase gene family, interleukin-1β-converting enzyme (ICE)/caspase 1 (Muzio et al., J. Biol. Chem., 1998, 273:2926–2930; Boldin et al., Cell, 1996, 85:803–815; Srinivasula et al., J. Biol. Chem., 1996, 271:27099–27106; Orth et al., J. Biol. Chem., 1996, 271: 20977–20980; Scaffidi et al., EMBO J., 1998, 17:1675–1687; Vincenz et al., J. Biol. Chem.,1997, 272: 6578–6583; and Schulz et al., 1994, Cell, 76:145–155). At least thirteen caspases have been identified thus far, and they are responsible for the proteolytic cascade that is essential for some aspects of apoptosis, including membrane blebbing and DNA degradation (Cryns et al., Genes and Devel., 1998, 12:1551–1570). Caspases 8, 9, and 10 are the only known members of this family that contain duplicated death effector domains (DEDs) in a long pro-domain in their amino terminus that precedes the cysteine protease catalytic domain in their carboxyl terminus. The DEDs allow caspase-8 to interact directly with an adaptor molecule, FADD, that also contains a DED. FADD, in turn, contains a death domain (DD) that allows it to directly associate with a number of cell death receptors (e.g., Fas, DR3).

Caspase-8, along with the adapter molecule FADD, is part of the death inducing signaling complex (DISC) associated with the Fas receptor (Medema, et al., EMBO J., 1997, 16:2794–2804). It is activated by autoproteolytic cleavage following recruitment to the receptor through its interaction with the DED of FADD, which allows caspase-8 to form aggregates (Scaffidi et al., EMBO J., 1998, 17:1675–1687; Yang et al., Molecular Cell, 1998, 1:319–325; Muzio et al., supra, 1998). These laboratories have shown that this oligomerization plays an important role in initiating the proper processing of the caspase itself, ultimately leading to an active caspase enzyme. Similarly, the DEDs of caspase 9 allow it to be recruited to a complex with Apafs 1 and 2, where its oligomerization leads to autocatalytic activation as well (Liu et al., Cell, 1997, 89:175–184; Srinivasula et al., supra, 1998). Thus, caspases 8 and 9 are located upstream of all other caspases and their effector function is responsible for the activation of the "caspase cascade", and subsequent cell death, that occurs following Fas/DR3/TNFR1 activation and release of cytochrome c from mitochondria. Such important apoptotic signaling molecules may be likely targets for disregulation/alteration during tumorigenesis.

SUMMARY OF THE INVENTION

The present invention relates to the discovery that CASP8 is inactivated in cancers, and plays a role of a tumor suppressor gene. Thus, the invention provides a method for detecting inactivation of a CASP8 gene. In particular, the method comprises detecting a modification of genomic DNA comprising the CASP8 gene, particularly the promoter, wherein such a modification results in inactivation of a CASP8 gene. This method is particularly useful for obtaining a diagnosis or prognosis of a cancer, particularly a neuroblastoma.

Thus, the invention further provides a method for diagnosis or prognosis of a cancer, particularly one associated with amplification of a MYC oncogene, comprising detecting inactivation of a CASP8 gene. According to the invention, inactivation of the CASP8 gene is indicative of the presence of a cancer or a poor prognosis for outcome of treatment of the cancer, at least by conventional therapies. In a preferred embodiment, detection of inactivation of CASP8 involves detecting methylation of the CASP8 promoter.

The invention further provides a nucleic acid comprising at least a part of the genomic gene encoding CASP8. In particular, the nucleic acid is a CASP8 genomic DNA;

a CASP8 promoter;

a nucleic acid amplified by primers that correspond to a sequence selected from the group consisting of SEQ ID NOS: 1, 2, 3, 4, 5, 6, 7, 8, 9, 10, 12, 13, 14, 15, 16, 17, 18, 19, 20, 21, 22, 23, 24, 25, 26, 27, and 28;

a CASP8 exon;

a CASP8 intron;

or a nucleic acid having at least 15 bases and hybridizable under stringent conditions to a CASP8 non-coding sequence.

In specific embodiments, the CASP8 genomic DNA comprises a nucleic acid sequence as depicted in SEQ ID NOS:3–10, and the CASP8 promoter comprises a nucleic acid sequence as depicted in SEQ ID NOS:1–2.

Furthermore, the invention provides a kit for detecting inactivation of a CASP8 gene comprising a detection assay, e.g., an immunoassay, PCR-based assay, or hybridization assay, for inactivation of a CASP8 gene. Preferably, a kit of the invention provides for detection of the methylation of the CASP8 promoter.

Having identified that inactivation of CASP8 plays a role in cancer, the invention provides a method of treating a cancer in a subject. The method comprises administering an amount of a vector that expresses a gene encoding functional CASP8 effective to express a functional level of CASP8 into cells of the subject, i.e., gene therapy.

Accordingly, the invention provides a vector, such as a defective virus (particularly a neurotrophic virus) or non-viral vector, that expresses a gene encoding functional human CASP8 in human target cells.

The method further comprises using such gene therapy in combination with other anti-cancer therapies. Having identified that CASP8 overexpression sensitizes cancer cells to doxorubicin-induced apoptosis, the invention preferably comprises using such gene therapy in combination with chemotherapy.

In addition to gene therapy, recognition of the role of inactivation of the CASP8 gene in cancer has led to discovery of a method of screening for a candidate compound that induces death-receptor-mediated apoptosis in cells where a CASP8 gene is inactivated. This method comprises contacting cells in which a CASP8 gene is inactivated with a candidate compound and detecting whether the cell undergoes apoptosis. An associated kit for screening for a candidate compound that induces death-receptor-mediated apoptosis in cells where a CASP8 gene is inactivated, comprising cells in which a CASP8 gene is inactivated and a detection assay for whether the cell undergoes apoptosis, is also provided.

The present invention will be better understood by reference to the Drawings, Detailed Description, and Examples, which follow.

DESCRIPTION OF THE DRAWINGS

FIGS. 2A and 2B. Southern blot analysis of total genomic DNA from three different neuroblastoma cell lines. Genomic DNA was subjected to restriction endonuclease digestion with either EcoRI or HindIII and then hybridized with the caspase-8 cDNA. This analysis revealed that both enzymes are associated with RFLPs. The arrows to the right of each panel indicate the different polymorphic fragments that hybridized with the cDNA probe. A: With EcoRI, an approximately 4.7 kb fragment loses an EcoRI site, generating an 8.8 kb fragment. B: With HindIII, a 4.0 kb fragment loses a HindIII restriction site, resulting in a new 7.2 kb fragment. The haplotype of the three cell lines for each of the enzymes is indicated below each panel. Size of genomic DNA in kb is indicated to the left of each panel.

FIGS. 6A and 6B. Methylation status of CASP8, and its effect on caspase-8 expression, in NB cell lines. A: 5-aza-cytidine treatment of NB10 and NB14 results in the expression of caspase-8. B:Methylation PCR analysis of the NB cell lines. The methylated primers detect only DNA that contain methylated CpG dinucleotides, whereas the unmethylated primers detect only DNA that contains no methylated CpG dinucleotides.

FIGS. 8A, 8B, 8C, 8D, and 8E. Effects of retrovirus expression of caspase-8 in three different NB cell lines that are caspase-8 nulls. A:Immunoblot demonstrating that caspase-8 (wild type) and caspase-8(DN) are expressed. The caspase-8(DN) product migrates at a higher molecular weight due to an HA-tag attached to its carboxyl-terminus. B, C:Morphology of NB7/Casp8 cells 5 hours after treatment with TNFα and cycloheximide. Membrane blebbing (Nomarski view, B) and condensed chromatin (visualized by DAPI staining, C), characteristics of apoptotic cells, are clearly visible. D:Percentage of cells that are positive for cell surface annexin-V staining, another hallmark of apoptotic cells. The various cell lines and their treatment regimens are shown at the bottom. E: Apoptotic induction by Fas mAb in proliferating NB8 and NB10 cells stably expressing caspase-8 at a low level. Induction measured as percentage of cells that are TUNEL-positive. The various cell lines and their treatment regimens are shown at the bottom.

DETAILED DESCRIPTION OF THE INVENTION

Figure 1:
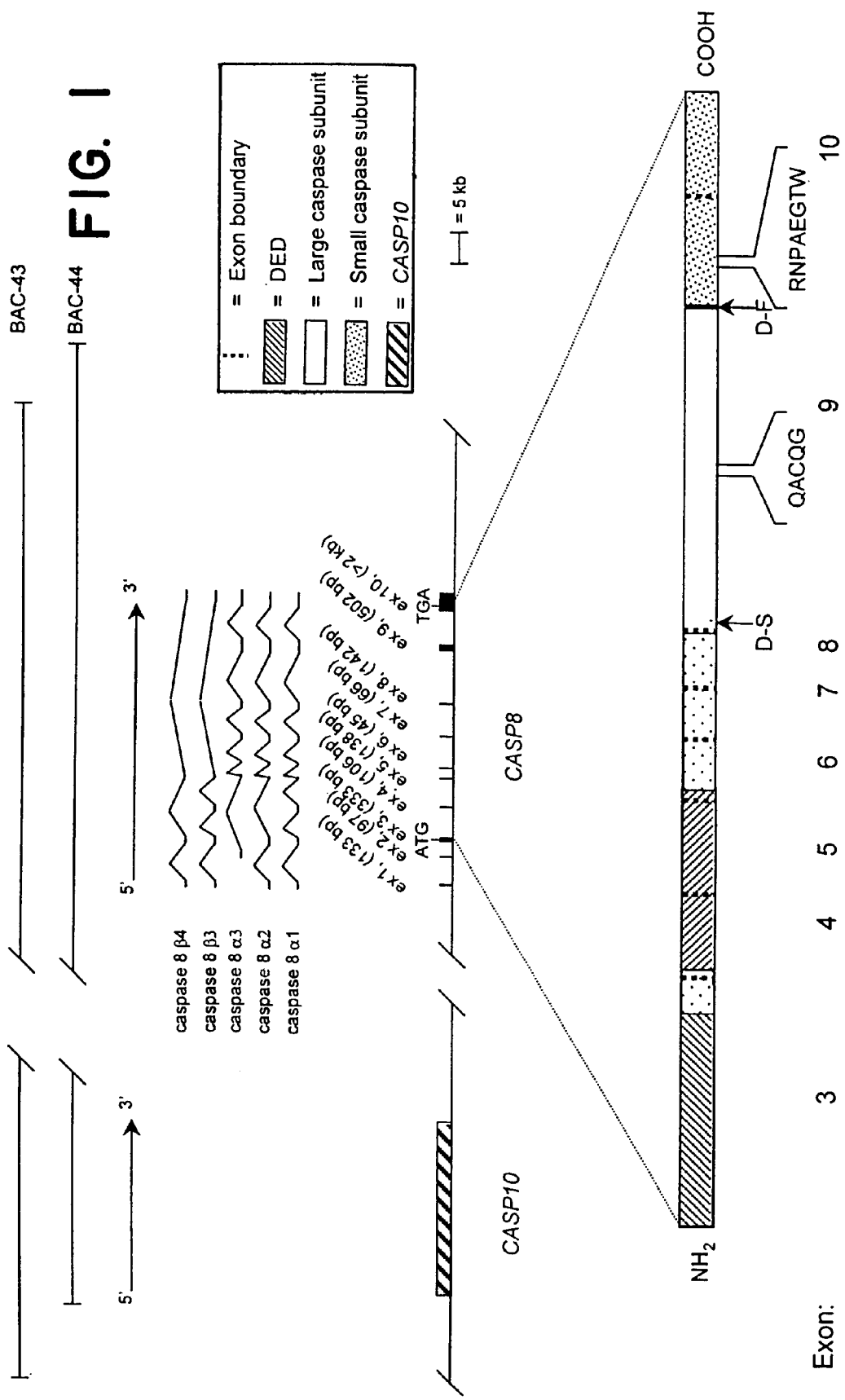
FIG. 1. Organization of the human CASP8 gene relative to the domain structure of the corresponding protein. TOP: The BAC-43 and BAC-44 clones, relative to the genomic segment containing CASP8, are shown. Five different CASP8 alternative splice products are also indicated above the gene, and they are designated according to Boldin et al. (Cell 85:803, 1996). CENTER: CASP8 gene organization. Vertical black bars delineate the coding exons, which are numbered sequentially with their size given in bp. The lines between the vertical black bars denote introns. CASP10 is shown upstream of CASP8. BOTTOM: Schematic of the caspase-8 domain structure compared to the organization of the gene shown above. Salient features to the protein, e.g., DEDs, caspase subunits, Asp-X cleavage sites (D-S and D-F), the catalytic cysteine residue (QACXG) (SEQ ID NO:11), and the substrate specificity motif (RNPAEGTW) (SEQ ID NO:12) are also shown.

The present invention is based, in part, on the surprising discovery that CASP8 is functionally inactivated in greater than 90% of all MYCN amplified neuroblastoma cell lines analyzed. Neuroblastoma is a pediatric solid tumor, and those cases with MYCN amplification have a particularly poor prognosis. Inactivation of CASP8 was observed to occur by homozygous deletion, heterozygous deletion coupled with gene silencing by methylation, and homozygous gene silencing by methylation. The data further show that the CASP10 gene, which is closely linked to CASP8, is not affected in a cell line containing the homozygous deletion. This discovery is significant in oncology, because cells in which caspase-8 is not expressed are not capable of undergoing apoptosis mediated by death receptors such as Fas and DR3. Furthermore, when caspase-8 expression is re-established in cell lines, either by microinjection or 5-aza-cytidine treatment, the cells undergo apoptosis. These data link caspases directly to tumorigenesis and suggest that CASP8 is a tumor suppressor, the first such gene identified in neuroblastoma.

Initial data also showed that inactivation of caspase-8 is prevalent in a subset of small-cell lung cancers. This type of cancer is associated with an amplified LMYC oncogene. It is likely that CASP8 is inactivated in other tumors as well, particularly when there is overexpression or amplification of MYC genes. Members of the MYC gene family include NMYC, LMYC, cMYC, etc.

The CASP8 promoter region sequences, in particular Region 1 (SEQ ID NO:1) and Region 2 (SEQ ID NO:2), which have not been previously characterized, are crucial to the design and execution of the genomic methylation PCR analysis of CASP8 gene inactivation. Methylation PCR can be used to examine even minute amounts of patient material to demonstrate whether the CASP8 gene expresses an mRNA and protein product. This method, and associated kits, are particularly preferred for evaluating CASP8 inactivation. In a specific embodiment, methylation PCR analysis can be performed with the primers of SEQ ID NOS: 29–34, as described in the Examples, infra. The promoter Region 1 sequence is located upstream (5') to exon 1, which is the alternatively-spliced 5' untranslated region that is less commonly used. The promoter Region 2 sequence is located downstream (3') of exon 1 and upstream of exon 2, which is the more commonly used 5' untranslated region.

As used herein, "inactivation of caspase-8" and "inactivation of CASP8 gene" are used interchangeably to refer to a modification of the genomic sequence of CASP8 that results in impairment of transcription or translation of the gene, or of activity of the gene product. For example, genomic methylation of the CASP8 promoter results in inactivation of that allele. Similarly, deletion of the segment of the chromosome containing CASP8, i.e., deletion of the CASP8 gene, results in inactivation of that allele of the gene. Inactivation of one allele may reduce the level of expression of caspase-8 to below that necessary for proper cellular regulation. No caspase-8 expression occurs with inactivation of both alleles by either or both mechanisms (or any of the other mechanisms discussed herein).

In addition to genomic methylation of the promoter and gene deletion, the term "modification of genomic DNA" refers to any mutation of the DNA that impairs gene expression or protein activity. For example, mutations that lead to insertion of a heterologous sequence in the gene, truncation of the gene, and introduction of a nonsense mutation, a frameshift mutation, a splice-site mutation, or a missense mutation can result in inactivation of the gene. Furthermore, point mutations (polymorphisms) can impact mRNA stability and translation efficiency, for example by introducing a base that affects secondary structure of the message. Other point mutations, for example in the caspase DED or catalytic domains, can lead to expression of an inactive protein. In the latter circumstance, protein expression may be detectable (e.g., by immunoassay), so only analysis of the CASP8 gene permits identification of an inactivating point mutation.

Cancers related to the present invention include solid tumors, including carcinomas, and non-solid tumors, including hematologic malignancies. Preferably, these tumors overexpress or evidence amplification of a MYC family gene. More preferably, caspase-8 is inactivated in these tumors. Examples of solid tumors according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias, lymphomas, and multiple myelomas. The following are non-limiting preferred examples of the cancers that can be diagnosed (including determination of a diagnosis or prognosis, or both) or treated in accordance with the present invention: neuroblastoma (particularly juvenile neuroblastoma), small-cell lung carcinoma, non-small-cell lung carcinoma, colorectal carcinoma, and uterine cervical carcinoma.

The invention advantageously involves the identification and characterization of the genomic sequence of CASP8 (SEQ ID NOS:3–10). The results show that the CASP8 gene contains at least 11 exons spanning approximately 30 kb on human chromosome band 2q33–34. This region of human chromosome 2 was previously reported as the location of the CASP10 gene, whose product is closely related to caspase-8. Chromosome 2 band q33–34 is also involved in tumorigenesis, with loss of heterogeneity (LOH) being reported in a number of tumors. The invention further results from identification of diagnostic restriction fragment polymorphisms; EcoRI and HindIII polymorphisms were discovered that may prove to be useful in disease analysis.

The specific following genomic sequences of CASP8 are provided:
    exon 3, flanked by partial sequences of introns 2 and 3
      SEQ ID NO:3
    exon 4, flanked by partial sequences of introns 3 and 4
      SEQ ID NO:4
    exon 5, flanked by partial sequences of introns 4 and 5
      SEQ ID NO:5 exon 6, flanked by partial sequences of introns 5 and 6
SEQ ID NO:6
exon 7, flanked by partial sequences of introns 6 and 7
SEQ ID NO:7
exon 8, flanked by partial sequences of introns 7 and 8
SEQ ID NO:8
exon 9, flanked by partial sequences of introns 8 and 9
SEQ ID NO:9
exon 10, flanked by partial sequences of introns 9 and 10
SEQ ID NO:10

Table 1, infra, identifies the intron-exon boundaries for these sequences. Caspase-8 is encoded by exons 3–10.

Abbreviations. The following abbreviations have been used: aa, amino acids; bp, base pairs; cDNA, DNA complementary to RNA; DD, death domain, DED, death effector domain; DISC, death-inducing signaling complex; FADD, Fas associated death domain; FISH, fluorescent in situ hybridization; ICE, interleukin-1β-converting enzyme; GFP, green fluorescent protein; kb(s), kilobase or 1000 bp; nt, nucleotide; oligo, oligodeoxyribonucleotide; ORF, open reading frame; RFLP, restriction fragment length polymorphism; SSC, 0.15M NaCl/0.015M Na, citrate pH7.6; UTR, untranslated region(s).

General Definitions

In a specific embodiment, the term "about" or "approximately" means within 20%, preferably within 10%, and more preferably within 5% of a given value or range. Alternatively, particularly with respect to biological systems or processes, the term means within an order of magnitude, and preferably a factor of two, of a value.

As used herein, the term "isolated" means that the referenced material is free of components present in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. A purified tumor cell is preferably substantially free of other normal cells. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The use of italics indicates a nucleic acid molecule (e.g., *CASP8*, *cDNA*, *gene*, etc.); normal text (e.g., CASP8 or caspase-8) indicates the polypeptide or protein.

CASP8 Nucleic Acids

The present invention contemplates isolation of a nucleic acids encoding a CASP8 of the invention, including a full length, or naturally occurring form of CASP8, and any antigenic fragments thereof from any source. Other nucleic acids encode all or part of a *CASP8* exon or intron, or both. In a specific embodiment, the invention provides a complete and partial *CASP8* genomic DNAs (SEQ ID NOS:3–10). In specific embodiments, clones BAC-43 (also termed herein CASP-43) and BAC-44 (also termed herein CASP-44), or clones having similar structure, contain the complete *CASP8* genomic gene. The invention also provides *CASP8* restriction fragments and restriction fragment polymorphisms, including, but by no means limited to, EcoRI fragments of 4.7 kb and about 8.0 kb, and HindIII fragments of 4.0 kb and about 7.2 kb. Polymorphic variants of *CASP8*, particularly polymorphisms (i.e., mutations) that result in inactivation of caspase-8, are also included. Furthermore, although the present invention relates to human *CASP8* nucleic acids, including allelic variants (e.g., as represented by the RFLPs noted above), in certain embodiments, such as for gene therapy, non-human variants of *CASP8* are contemplated.

In a further embodiment, the invention provides Regions 1 (SEQ ID NO:1) and 2 (SEQ ID NO:2) of the *CASP8* promoter. Considered from the 5' to 3' direction, these two regions flank exon 1 (a 5' UTR that is less commonly used), and exons 1 and 2 (the alternatively spliced 5' UTR that is more commonly used) flank promoter Region 2. Also provided are oligonucleotides that hybridize to the promoters, and particularly to methylated or unmethylated forms of the promoters. In a specific embodiment, these oligonucleotides are PCR primer pairs having sequences as depicted in SEQ ID NOS:29–34, as described in Example 3, infra.

In accordance with the present invention there may be employed conventional molecular biology, microbiology, and recombinant DNA techniques within the skill of the art. Such techniques are explained fully in the literature, e.g., in Sambrook, Fritsch and Maniatis, *Molecular Cloning. A Laboratory Manual*, Second Edition, 1989, Cold Spring Harbor Laboratory Press: Cold Spring Harbor, N.Y. (herein "Sambrook et al., 1989"); *DNA Cloning. A Practical Approach*, Volumes I and II, D. N. Glover ed., 1985; *Oligonucleotide Synthesis*, M. J. Gait ed., 1984; *Nucleic Acid Hybridization*, B. D. Hames and S. J. Higgins eds., 1985; *Transcription And Translation*, B. D. Hames and S. J. Higgins eds., 1984; *Animal Cell Culture*, R. I. Freshney ed., 1986; *Immobilized Cells And Enzymes*, IRL Press, 1986; B. Perbal, *A Practical Guide To Molecular Cloning*, 1984; *Current Protocols in Molecular Biology*, F. M. Ausubel et al. eds., John Wiley and Sons, Inc., 1994.

Therefore, if appearing herein, the following terms shall have the definitions set out below.

A "vector" is a recombinant nucleic acid construct, such as plasmid, phage genome, virus genome, cosmid, or artificial chromosome, to which another DNA segment may be attached. In a specific embodiment, the vector may bring about the replication of the attached segment, e.g., in the case of a cloning vector. A "replicon" is any genetic element (e.g., plasmid, chromosome, virus) that functions as an autonomous unit of DNA replication in vivo, i.e., it is capable of replication under its own control. The term "vector" includes both viral and nonviral means for introducing the nucleic acid into a cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors, as set forth in greater detail below. In addition to a nucleic acid according to the invention, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA is expressed and effects a function or phenotype on the cell in which it is expressed.

The term "heterologous" refers to a combination of elements not naturally occurring. For example, heterologous DNA refers to DNA not naturally located in the cell, or in a chromosomal site of the cell. A heterologous expression regulatory element is a such an element operatively associated with a different gene than the one it is operatively associated with in nature, such as a CMV promoter operatively associated with a CASP8 coding region. In the context of the present invention, an CASP8 gene is heterologous to vector DNA in which it is inserted for cloning or expression.

A "nucleic acid molecule" (or alternatively "nucleic acid") refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

The present invention provides antisense nucleic acids (including ribozymes), which may be used as probes or to inhibit expression of CASP8. An "antisense nucleic acid" is a single stranded nucleic acid molecule which, on hybridizing with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA—RNA interactions, RNA-DNA interactions, ribozymes, and RNase-H mediated arrest. Antisense nucleic acid molecules can be encoded by a recombinant gene for expression in a cell (e.g., U.S. Pat. Nos. 5,814,500 and 5,811,234), or alternatively they can be prepared synthetically (e.g., U.S. Pat. No. 5,780,607).

Specific examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—N$(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science, 1991, 254:1497). Other synthetic oligonucleotides may contain substituted sugar moieties comprising one of the following at the 2' position: OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

A "gene" is used herein to refer to a portion of a DNA molecule that includes a polypeptide coding sequence operatively associated with expression control sequences. Thus, a gene includes both transcribed and untranscribed regions. The transcribed region may include introns, which are spliced out of the mRNA, and 5'- and 3'-untranslated (UTR) sequences along with protein coding sequences. In one embodiment, a gene can be a genomic or partial genomic sequence, in that it contains one or more introns. In another embodiment, the term gene may refer to a cDNA molecule (i.e., the coding sequence lacking introns).

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a translation start codon at the 5' (amino) terminus and a translation stop codon at the 3' (carboxyl) terminus.

"Expression control sequences", e.g., transcriptional and translational control sequences, are regulatory sequences that flank a coding sequence, such as promoters, enhancers, suppressors, terminators, and the like, and that provide for the expression of a coding sequence in a host cell. In eukaryotic cells, a polyadenylation signal and transcription termination sequence will usually be located 3' to the coding sequence. On mRNA, a ribosome binding site is an expression control sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if it contains introns) and translated into the protein encoded by the coding sequence.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., 1989, 9.50–9.51). For hybridization with shorter nucleic acids, i.e., oligonucleotides, the position of mismatches becomes more important, and the length of the oligonucleotide determines its specificity (see Sambrook et al., 1989, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a ligand molecule, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR or sequencing primers, either for cloning full length or a fragment of CASP8, or to detect the presence of nucleic acids encoding CASP8. In a further embodiment, an oligonucleotide of the invention can form a triple helix with a CASP8 DNA molecule. In still another embodiment, a library of oligonucleotides arranged on a solid support, such as a silicon wafer or chip, can be used to detect various CASP8 polymorphisms of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell, 1987, 50:667). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 30%, and preferably at least about 50%, of the nucleotides match over the defined length of the DNA sequences. An example of such a sequence is an allelic variant of the specific CASP8 genes of the invention. Sequences that are substantially homologous can be identified by comparing the sequences using standard software available in sequence data banks or from commercial sources (BLAST, DNA Strider, DNA Star, FASTA, etc.) using standard or default parameters, or in a Southern hybridization experiment under, for example, stringent conditions as defined for that particular system. Defining appropriate hybridization conditions is within the skill of the art. See, e.g., Sambrook et al., 1989; *DNA Cloning*, Vols. I & II, supra; *Nucleic Acid Hybridization*, supra.

Similarly, in a particular embodiment, two amino acid sequences are "substantially homologous" or "substantially similar" when greater than about 80%, preferably greater than about 90%, of the amino acids are identical, or greater than about 85%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the sequence alignment programs described above.

A gene encoding CASP8, whether genomic DNA or cDNA, can be isolated from any source, particularly from a human cDNA or genomic library. Methods for obtaining CASP8 gene are well known in the art, as described above (see, e.g., Sambrook et al., 1989). The DNA may be obtained by standard procedures known in the art from cloned DNA (e.g., a DNA "library"), and preferably is obtained from a cDNA library prepared from tissues with high level expression of the protein (e.g., a peripheral blood leukocyte cell library, since these are the cells that evidence high levels of expression of CASP8), by chemical synthesis, by cDNA cloning, or by the cloning of genomic DNA, or fragments thereof, purified from the desired cell (see, e.g., Sambrook et al., 1989; DNA cloning, supra). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Identification of the specific DNA fragment containing the desired CASP8 gene may be accomplished in a number of ways. For example, a portion of a CASP8 gene exemplified infra can be purified and labeled to prepare a labeled probe, and the generated DNA may be screened by nucleic acid hybridization to the labeled probe (Benton and Davis, Science, 1977, 196:180; Grunstein and Hogness, Proc. Natl. Acad. Sci. USA, 1975, 72:3961). Those DNA fragments with substantial homology to the probe, such as an allelic variant from another individual, will hybridize. In a specific embodiment, highest stringency hybridization conditions are used to identify a homologous CASP8 gene.

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of CASP8 protein as disclosed herein. Thus, the presence of the gene may be detected by assays based on the physical, chemical, immunological, or functional properties of its expressed product.

The present invention also relates to cloning vectors containing genes encoding analogs and derivatives of CASP8 of the invention, that have the same or homologous functional activity as CASP8. The production and use of derivatives and analogs related to CASP8 are within the scope of the present invention. In a specific embodiment, the derivative or analog is functionally active, i.e., capable of exhibiting one or more functional activities associated with a full-length, wild-type CASP8 of the invention. Such functions include FADD and death receptor binding, induction of apoptosis, autoproteolytic cleavage, and aggregate formation. Chimeric fusion proteins with CASP8, such as GST or HIS-tagged CASP8, are contemplated, as are fusion proteins that contain functional domains (discussed below).

CASP8 derivatives can be made by altering encoding nucleic acid sequences by substitutions, additions or deletions that provide for functionally equivalent molecules. Preferably, derivatives are made that have enhanced or increased functional activity relative to native CASP8. For example, chimeric derivatives with a greater self-aggregation potential, e.g., prepared by incorporating an additional of stronger aggregation sequence, may have increased functional activity. Alternatively, a chimeric CASP8 protein that contains the FADD death domain may be especially effective for generation of a death-inducing signaling complex, even in the absence of FADD.

Due to the degeneracy of nucleotide coding sequences, other DNA sequences which encode substantially the same amino acid sequence as a CASP8 gene may be used in the practice of the present invention. These include but are not limited to allelic genes and nucleotide sequences comprising all or portions of CASP8 genes which are altered by the substitution of different codons that encode the same amino acid residue within the sequence, thus producing a silent change. Likewise, the CASP8 derivatives of the invention include, but are not limited to, those containing, as a primary amino acid sequence, all or part of the amino acid sequence of a CASP8 protein including altered sequences in which functionally equivalent amino acid residues are substituted for residues within the sequence resulting in a conservative amino acid substitution. For example, one or more amino acid residues within the sequence can be substituted by another amino acid of a similar polarity and, if present, charge, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

The genes encoding CASP8 derivatives and analogs of the invention can be produced by various methods known in the art. The sequence can be cleaved at appropriate sites with restriction endonuclease(s), followed by further enzymatic modification if desired, isolated, and ligated in vitro. In the production of the gene encoding a derivative or analog of CASP8, care should be taken to ensure that the modified gene remains within the same translational reading frame as the CASP8 gene, uninterrupted by translational stop signals, in the gene region where the desired activity is encoded.

Additionally, the CASP8-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., J. Biol. Chem., 1978, 253:6551; Zoller and Smith, DNA, 1984, 3:479–488; Oliphant et al., Gene, 1986, 44:177; Hutchinson et al., Proc. Natl. Acad. Sci. USA, 1986, 83:710), use of TAB linkers (Pharmacia), etc. PCR techniques are preferred for site directed mutagenesis (see Higuchi, in PCR *Technology: Principles and Applications for DNA Amplification*, H. Erlich ed., Stockton Press, 1989, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 μ plasmid.

CASP8 Polypeptides

The nucleotide sequence coding for CASP8, including derivatives or analogs thereof, or a functionally active chimeric protein thereof (herein collectively "caspase-8" or "CASP8"), can be inserted into an appropriate expression vector, i.e., a vector which contains the necessary elements for the transcription and translation of the inserted protein-coding sequence in vivo. Thus, the nucleic acid encoding CASP8 of the invention is operationally associated with a promoter in an expression vector of the invention. Both cDNA and genomic sequences can be cloned and expressed under control of such regulatory sequences. An expression vector also preferably includes a replication origin.

Alternatively, an CASP8 polypeptide of the invention can be prepared using well-known techniques in peptide synthesis, including solid phase synthesis (using, e.g., BOC of FMOC chemistry), or peptide condensation techniques.

As used herein, the terms "polypeptide" and "protein" may be used interchangeably to refer to the gene product (or corresponding synthetic product) of a CASP8 gene. The term "protein" may also refer specifically to the polypeptide as expressed in cells. A peptide is generally a fragment of a polypeptide, e.g., of about six or more amino acid residues.

The necessary transcriptional and translational signals can be provided on a recombinant expression vector, or they may be supplied by the native gene encoding CASP8 and/or its flanking regions. Preferably, such control sequences, whether a promoter or enhancer, or both, permit high level expression of caspase-8 in the target cell, particularly for gene therapy (described infra).

Potential host-vector systems include but are not limited to mammalian cell systems infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities.

Depending on the host-vector system utilized, any one of a number of suitable transcription and translation elements may be used.

A recombinant CASP8 protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989).

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of CASP8 protein may be controlled by any promoter/enhancer element known in the art, but these regulatory elements must be functional in the host selected for expression. In one embodiment, the promoter permits high level expression in a mammalian, and more preferably human, host cell. For example, viral promoters, some of which are listed below, often permit high level expression. Other such promoters are known. Promoters which may be used to control CASP8 gene expression include, but are not limited to, cytomegalovirus (CMV) promoter (U.S. Pat. Nos. 5,168,062 and 5,385,839), the SV40 early promoter region (Benoist and Chambon, Nature, 1981, 290:304–310), the promoter contained in the 3' long terminal repeat of Rous sarcoma virus (Yamamoto, et al., Cell, 1980, 22:787–797), the herpes thymidine kinase promoter (Wagner et al., Proc. Natl. Acad. Sci. USA, 1981, 78:1441–1445), the regulatory sequences of the metallothionein gene (Brinster et al., Nature, 1982, 296:39–42); prokaryotic expression vectors such as the β-lactamase promoter (Villa-Kamaroff, et al., *Proc. Natl. Acad. Sci*. USA, 1978, 75:3727–3731), or the tac promoter (DeBoer, et al., *Proc. Natl. Acad. Sci*. USA, 1983, 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., Cell, 1984, 38:639–646; Ornitz et al., Cold Spring Harbor Symp. Quant. Biol., 1986, 50:399–409; MacDonald, Hepatology, 1987, 7:425–515); insulin gene control region which is active in pancreatic beta cells (Hanahan, Nature, 1985, 315:115–122), immunoglobulin gene control region which is active in lymphoid cells (Grosschedl et al., Cell, 1984, 38:647–658; Adames et al., Nature, 1985, 318:533–538; Alexander et al., Mol. Cell. Biol., 1987, 7:1436–1444), mouse mammary tumor virus control region which is active in testicular, breast, lymphoid and mast cells (Leder et al., Cell, 1986, 45:485–495), albumin gene control region which is active in liver (Pinkert et al., Genes and Devel., 1987, 1:268–276), alpha-fetoprotein gene control region which is active in liver (Krumlauf et al., Mol. Cell. Biol., 1985, 5:1639–1648; Hammer et al., Science, 1987, 235:53–58), alpha 1-antitrypsin gene control region which is active in the liver (Kelsey et al., Genes and Devel., 1987, 1:161–171), beta-globin gene control region which is active in myeloid cells (Mogram et al., Nature, 1985, 315:338–340; Kollias et al., Cell, 1986, 46:89–94), myelin basic protein gene control region which is active in oligodendrocyte cells in the brain (Readhead et al., Cell, 1987, 48:703–712), myosin light chain-2 gene control region which is active in skeletal muscle (Sani, Nature, 1985, 314:283–286), and gonadotropic releasing hormone gene control region which is active in the hypothalamus (Mason et al., Science, 1986, 234:1372–1378). Other promoters useful for practice of this invention are ubiquitous promoters (e.g., HPRT, vimentin, actin, tubulin), intermediate filament promoters (e.g., desmin, neurofilaments, keratin, GFAP), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, retroviral LTR, metallothionein, E1a, and MLP promoters. Tetracycline-regulated transcriptional modulators are described in PCT Publication No. WO 96/01313.

In a specific embodiment, promoters specific for expression in cells of the CNS can be used, e.g., for gene therapy of neuroblastoma or another CNS tumor. For example, the promoters for the human tyrosine hydroxylase gene (Kim et al., Nucl. Acids Res., 1998, 26:1793–800), human dopamine beta-hydroxylase (DBH) gene (Zellmer et al., J. of Neurosci., 1995, 15:8109–20) and human ENC-1 gene (Hernandez et al., Exp. Cell Res., 1998, 242:470–7) are CNS-specific.

Vectors are introduced into the desired host cells by methods known in the art, e.g., transfection, electroporation, microinjection, transduction, cell fusion, DEAE dextran, calcium phosphate precipitation, lipofection (liposome fusion), use of a gene gun, or a DNA vector transporter (see, e.g., Wu et al., J. Biol. Chem., 1992, 267:963–967; Wu and Wu, J. Biol. Chem., 1988, 263:14621–14624; Canadian Patent Application No. 2,012,311).

Antibodies to CASP8

According to the invention, CASP8 polypeptides, whether produced recombinantly or by chemical synthesis or purified from cells that express the protein endogenously, and fragments or other derivatives or analogs thereof, including fusion proteins, may be used as an immunogen to generate antibodies that recognize the CASP8 polypeptide. Such antibodies include but are not limited to polyclonal, monoclonal, chimeric, single chain, Fab fragments, and an Fab expression library. Such an antibody is specific for human CASP8.

Various procedures known in the art may be used for the production of polyclonal antibodies to CASP8 polypeptide or derivative or analog thereof. For the production of antibody, various host animals can be immunized by injection with the CASP8 polypeptide, or a derivative (e.g., fragment or fusion protein) thereof, including but not limited to rabbits, mice, rats, sheep, goats, etc. In one embodiment, the CASP8 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the CASP8 polypeptide, or fragment, analog, or derivative thereof, any technique that provides for the production of antibody molecules by continuous cell lines in culture may be used. These include but are not limited to the hybridoma technique originally developed by Kohler and Milstein (Nature, 1975, 256:495–497), as well as the trioma technique, the human B-cell hybridoma technique (Kozbor et al., Immunology Today, 1983, 4:72; Cote et al., Proc. Natl. Acad. Sci. USA, 1983, 80:2026–2030), and the EBV-hybridoma technique to produce human monoclonal antibodies (Cole et al., in Monoclonal Antibodies and Cancer Therapy, Alan R. Liss, Inc., pp. 77–96, 1985). Production of human antibodies by CDR grafting is described in U.S. Pat. Nos. 5,585,089, 5,693,761, 5,693,762, and 5,225,539, and PCT Publication No. WO91/09967. In an additional embodiment of the invention, monoclonal antibodies can be produced in germ-free animals (PCT Publication No. WO 89/12690). In fact, according to the invention, techniques developed for the production of "chimeric antibodies" (Morrison et al., J. Bacteriol., 1984, 159:870); Neuberger et al., Nature, 1984, 312:604–608; Takeda et al., Nature, 1985, 314:452–454) by splicing the genes from a mouse antibody molecule specific for an CASP8 polypeptide together with genes from a human antibody molecule of appropriate biological activity can be used; such antibodies are within the scope of this invention.

According to the invention, techniques described for the production of single chain antibodies (U.S. Pat. Nos. 5,476,786, 5,132,405, and 4,946,778) can be adapted to produce CASP8 polypeptide-specific single chain antibodies. An additional embodiment of the invention utilizes the techniques described for the construction of Fab expression libraries (Huse et al., Science, 1989, 246:1275–1281) to allow rapid and easy identification of monoclonal Fab fragments with the desired specificity for an CASP8 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an CASP8 polypeptide, one may assay generated hybridomas for a product which binds to an CASP8 polypeptide fragment containing such epitope.

The foregoing antibodies can be used in methods known in the art relating to the localization and activity of the CASP8 polypeptide, e.g., for Western blotting, imaging CASP8 polypeptide in situ, measuring levels thereof in appropriate physiological samples, etc. using any of the detection techniques mentioned above or known in the art. Such antibodies may exhibit surprisingly superior properties in immunodiagnostic (or immunoprognostic) assays for CASP8.

Diagnostics

The present invention provides for evaluating cancer in a subject or patient based on detecting whether caspase-8 has been inactivated. This evaluation can provide either a diagnosis or a prognosis, or both. For example, detecting inactivation of caspase-8 in neuroblastoma provides a diagnosis of aggressive neuroblastoma, and a prognosis of a poor outcome from traditional therapies.

The term "diagnosis" in any grammatical form refers to the identification of a particular disease condition in a subject or patient. As the skilled physician knows, almost any diagnosis is based on a multiple of determinants, including symptomology, histology, and other criteria, which together form a diagnosis. Thus, when used herein, diagnosis according to the invention is one component or determinant of the final diagnosis. The term "prognosis" in any grammatical form refers to prediction of a disease outcome, e.g., whether the subject suffering from the disease is likely to improve or regress.

Any form of cancer, e.g., as discussed above, can be evaluated using the diagnostic methods of the invention. Preferably, the cancer is neuroblastoma (particularly juvenile neuroblastoma), small-cell lung carcinoma, non-small-cell lung carcinoma, colorectal carcinoma, or uterine cervical carcinoma.

Various methods are known in the art for evaluating inactivation of caspase-8, either by nucleic acid based assays or protein based assays. These methods are discussed in greater detail below. In addition, the components useful in practicing the diagnostic and prognostic aspects of the invention can be conveniently provided in kit form, as set forth in greater detail below. Such kits contain, at least, a detection assay for inactivation of caspase-8.

Nucleic Acid Assays and Kits

Nucleic acid assays for inactivation of CASP8 are based on detection of mutations or modifications in the CASP8 gene that result in its inactivation. The DNA may be obtained from any cell source. Non-limiting examples of cell sources available in clinical practice include without limitation blood cells, buccal cells, cervicovaginal cells, epithelial cells from urine, fetal cells, or any cells present in tissue obtained by biopsy. Cells may also be obtained from body fluids, including without limitation blood, plasma, serum, lymph, milk, cerebrospinal fluid, saliva, sweat, urine, feces, and tissue exudates (e.g., pus) at a site of infection or inflammation. DNA is extracted from the cell source or body fluid using any of the numerous methods that are standard in the art. It will be understood that the particular method used to extract DNA will depend on the nature of the source. Generally, the minimum amount of DNA to be extracted for use in the present invention is about 25 pg (corresponding to about 5 cell equivalents of a genome size of $4 \times 10^9$ base pairs).

Modifications of the CASP8 genomic DNA include genomic methylation of the promoter. In a preferred aspect of the invention, evaluation of inactivation of CASP8 involves an assay for methylation of the CASP8 promoter. It has been found that in most cases, inactivation of CASP8 results from methylation of the promoter and not from gene deletion (see Examples 2, 3, infra). In a specific embodiment, methylation of the promoter can be detected by a methylation polymerase chain reaction (PCR) assay (see Belinsky et al., Proc. Natl. Acad. Sci. USA, 1998, 95:11891; Merlo et al., Nature Medicine, 1995, 1:686), preferably using primers designed based on the promoter regions depicted in SEQ ID NOS: 1 and 2. In a specific embodiment, primer pairs can be used to detect methylated, bisulfite treated promoter DNA (e.g., SEQ ID NOS:29 and 30), unmethylated, bisulfite-treated promoter DNA (e.g., SEQ ID NOS:31 and 32), and wild-type (un-bisulfite treated) DNA (e.g., SEQ ID NOS:33 and 34). A major advantage of this method is that it can be used to evaluate a small number of tumor cells isolated from patient tissue, even if they are contaminated with normal cells.

Mutations include an insertion in the gene, deletion of the gene, truncation of the gene (e.g., due to a nonsense, missense, or frameshift mutation), or disregulation of gene expression (e.g., due to a frameshift mutation or a splice-site mutation). In a specific embodiment, infra, CASP8 is heterozygously or homozygously deleted from chromosome 2. Identification of gene deletion is readily accomplished using nucleic acid probes or PCR analysis. Determination of polymorphic positions is achieved by any means known in the art, including but not limited to direct sequencing, hybridization with allele-specific oligonucleotides, allele-specific PCR, ligase-PCR, HOT cleavage, denaturing gradient gel electrophoresis (DGGE), and single-stranded conformational polymorphism (SSCP). Direct sequencing may be accomplished by any method, including without limitation chemical sequencing, using the Maxam-Gilbert method; by enzymatic sequencing, using the Sanger method; mass spectrometry sequencing; and sequencing using a chip-based technology (see, e.g., Little et al., Genet. Anal., 1996, 6:151). Preferably, DNA from a subject is first subjected to amplification by polymerase chain reaction (PCR) using specific amplification primers.

Gene expression, or lack of gene expression, can be directly evaluated by detecting CASP8 mRNA. Methods for detecting mRNA include Northern blotting and reverse transcriptase (RT)-PCR. These methods can be used to determine whether or not expression occurs, and whether a truncated (or oversized) message is expressed. All of these factors can help establish inactivation of caspase-8.

A nucleic acid assay kit of the invention will comprise a nucleic acid that specifically hybridizes under stringent conditions to a CASP8 gene, and an assay detector, e.g., a label. Where the kit is a PCR-based kit, a primer pair will be included; in this case, the detector may simply be a reagent such as ethidium bromide to quantify amplified DNA. In a preferred embodiment, a nucleic acid based kit of the invention includes primer pairs for PCR analysis of CASP8 promoter methylation. In a more preferred embodiment, the kit contains primer pairs that can be used to detect methylated, bisulfite treated promoter DNA (e.g., SEQ ID NOS:29 and 30), unmethylated, bisulfite-treated promoter DNA (e.g., SEQ ID NOS:31 and 32), and wild-type (un-bisulfite treated) DNA (e.g., SEQ ID NOS:33 and 34). Optional components include buffer or buffer reagents, nucleotides, and instructions for use of the kit. If possible, a positive control is also included, e.g., a probe or primer pair for an endogenously expressed gene, such as actin or tubulin.

Protein Based Assays

As an alternative to analyzing CASP8 nucleic acids, one can evaluate caspase-8 on the basis of protein expression. Indeed, this assay may be the most informative, since CASP8 mRNA levels may appear high, but a mutation in the sequence may make the mRNA less effective for translation, resulting in reduction or elimination of protein expression.

In a preferred embodiment, caspase-8 is detected by immunoassay. For example, as exemplified infra, Western blotting permits detection of the presence or absence of caspase-8. Other immunoassay formats, e.g., as discussed above in connection with CASP8-specific antibodies, can also be used in place of Western blotting.

Alternatively, a biochemical assay can be used to detect expression of caspase-8, e.g., by the presence or absence of a band by polyacrylamide gel electrophoresis; by the presence or absence of a chromatographic peak by any of the various methods of high performance liquid chromatography, including reverse phase, ion exchange, and gel permeation; by the presence or absence of caspase-8 in analytical capillary electrophoresis chromatography, or any other quantitative or qualitative biochemical technique known in the art.

For both kinds of assays, biopsy tissue is obtained from a subject. The tumor cells should be purified from other tissue to ensure that contaminating CASP8 from normal cells is not detected. Antibodies that are capable of binding to caspase-8 are then contacted with samples of the tissue under conditions that permit antibody binding to determine the presence or absence of caspase-8. In a further embodiment, antibodies that distinguish polymorphic variants of caspase-8 can be used. The antibodies may be polyclonal or monoclonal, preferably monoclonal.

Measurement of specific antibody binding to cells may be accomplished by any known method, e.g., quantitative flow cytometry, or enzyme-linked or fluorescence-linked immunoassay. The presence or absence of a particular mutation, and its allelic distribution (i.e., homozygosity vs. heterozygosity) is determined by comparing the values obtained from a patient with norms established from populations of patients having known polymorphic patterns.

The components for detecting caspase-8 protein can be conveniently provided in a kit form. In its simplest embodiment, a kit of the invention provides a caspase-8 detector, e.g., a detectable antibody (which may be directly labeled or which may be detected with a secondary labeled reagent).

Anti-Tumor Gene Therapy

The term "anti-tumor gene therapy" as used herein refers to a gene therapy targeted to cells of a tumor, i.e., cancer, which causes tumor necrosis, apoptosis, growth regulation, i.e., regression or suppression of the tumor. In the practice of the present invention, anti-tumor gene therapy refers to administration or delivery of a gene encoding caspase-8, either alone or in combination with other genes effective for treating tumors.

Examples of anti-tumor gene therapies of the prior art include, but are by no means limited to, introduction of a suicide gene; introduction of an apoptosis gene; introduction of a tumor suppresser gene; and introduction of an oncogene antagonist gene. Preferably anti-tumor genes, such as CASP8, are supplemented with immunostimulatory genes to enhance recruitment and activation of immune effector cells. If a viral, such as adenovirus, vector is used (see, e.g., PCT Publication No. WO 95/14101), the presence of adenoviral antigens could also provide an adjuvant effect to overall enhanced immune responsiveness.

"Gene therapy" refers to transfer of a gene encoding an effector molecule into cells, in this case of the tumor. Gene therapy vectors include, but are not limited to, viral vectors (including retroviruses and DNA viruses), naked DNA vectors, and DNA-transfection agent admixtures. Preferably, a therapeutically effective amount of the vectors are delivered in a pharmaceutically acceptable carrier. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host, e.g., tumor progression, metastasises, or progression to the next stage of cancer. Alternatively, a therapeutically effective amount is sufficient to cause an improvement in a clinically significant condition in the host, e.g., to induce remission, reduce tumor size or burden, or both, or increase the time from treatment until relapse. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. Such methods, including routes of administration and dose, are well known in the art. These are discussed in greater detail in a section directed to "Gene Therapy Vectors" below, as well as in the references disclosed therein.

Gene therapy in accordance with the invention can be used to treat any cancer, but particularly tumors with an amplified MYC oncogene. Preferably, caspase-8 is inactivated in the tumor cells of the cancer. However, this does not necessarily have to be the case: increasing the level of expression of caspase-8 beyond endogenous levels is expected to initiate cell death-inducing signaling. Alternatively, modified forms of caspase-8 (discussed supra) with enhanced death-inducing activity can be used in tumor cells that express wild-type caspase-8 endogenously. Furthermore, assays that detect expression (e.g., Northern assays) or translation (e.g., immunoassays) of CASP8 may not differentiate a defective gene product from wild-type, thus delivery of the wild-type gene may be useful even if it appears that the cell expresses caspase-8.

As noted above, caspase-8 gene therapy of a tumor can be combined with other anti-tumor therapies, including but by no means limited to suicide gene therapy, anti-oncogene or tumor suppressor gene therapy, administration of tumor growth inhibitors, administration of angiogenesis inhibitors, immune therapies with an immunologically active polypeptide (including immunostimulation, e.g., in which the active polypeptide is a cytokine, lymphokine, or chemokine, and vaccination, in which the active polypeptide is a tumor specific or tumor associated antigen), and conventional cancer therapies (chemotherapy and radiation therapy).

Suicide gene therapies. Introduction of genes that encode enzymes capable of conferring to tumor cells sensitivity to chemotherapeutic agents (suicide gene) has proven to be an effective anti-tumor gene therapy. A representative example of such a suicide gene is thymidine kinase of herpes simplex virus. Additional examples are thymidine kinase of varicella zoster virus and the bacterial gene cytosine deaminase which can convert 5-fluorocytosine to the highly toxic compound 5-fluorouracil.

The prodrug useful in the methods of the present invention is any that can be converted to a toxic product, i.e., toxic to tumor cells. The prodrug is converted to a toxic product by the gene product of the therapeutic nucleic acid sequence in the vector useful in the method of the present invention. Representative examples of such a prodrug is ganciclovir, which is converted in vivo to a toxic compound by HSV-tk. Other representative examples of pro-drugs include acyclovir, FIAU [1-(2-deoxy-2-fluoro-β-D-arabinofuranosyl)-5-iodouracil], 6-methoxypurine arabino-side for VZV-tk, and 5-fluorocytosine for cytosine deambinase.

Anti-oncogene and tumor suppresser gene therapies. Tumor initiation and progression in many cancer types are linked to mutations in oncogenes (e.g., ras, myc) and tumor suppresser genes (e.g., retinoblastoma protein, p53). A number of approaches are being pursued using anti-oncogene molecules including monoclonal antibodies, single chain antibody vectors, antisense oligonucleotide constructs, ribozymes and immunogenic peptides (Chen, Mol. Med. Today, 1997, 3:160–167; Spitz, et al., Anticancer Res., 1996, 16:3415–3422; Indolfi et al., Nat. Med., 1996, 2:634–635; Kijima et al., Pharmacol. Ther., 1995, 68:247–267). Various strategies can be employed for tumor suppressor gene therapy, particularly with p53 (PCT Publication No. WO 94/24297) or analogues thereof such as CTS-1 (French Patent Application No. FR 08729).

Gene Therapy Vectors

As discussed above, a vector is any means for the transfer of a nucleic acid according to the invention into a host cell. Preferred vectors for transient expression are viral vectors, such as retroviruses, herpes viruses, adenoviruses and adeno-associated viruses. Thus, a gene encoding a functional caspase-8 protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication No. WO 95/28494.

Viral vectors. Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 1992, 7:980–990). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV 1) vector (Kaplitt et al., Molec. Cell. Neurosci., 1991, 2:320–330), defective herpes virus vector lacking a glyco-protein L gene (Patent Publication RD 371005 A), or other defective herpes virus vectors (PCT Publication Nos. WO 94/21807 and WO 92/05263); an attenuated adenovirus vector, such as the vector described by Stratford-Perricaudet et al. (J. Clin. Invest., 1992, 90:626–630; see also La Salle et al., Science, 1993, 259:988–990); and a defective adeno-associated virus vector (Samulski et al., J. Virol., 1987, 61:3096–3101; Samulski et al., J. Virol., 1989, 63:3822–3828; Lebkowski et al., Mol. Cell. Biol., 1988, 8:3988–3996).

A defective herpes simplex virus has been shown to be effective for delivery of genes, particularly to cells of the CNS (see, e.g., Belloni et al., Human Gene Therapy, 1996, 7:2015–24).

Recombinant defective adenoviruses have been used for transferring foreign genes into cells, particularly for gene therapy of tumors (as noted above), and for delivery of therapeutic genes to cells of the central nervous system. For example, PCT Publication Nos.WO 94/08026 and WO 94/08026 describe recombinant adenovirus vectors for the transfer of foreign genes into the central nervous system (CNS). Other examples of gene delivery to the CNS include the following: French Publication No. FR2717824 discloses adenoviruses containing DNA from glial derived neutrophilic factors, which infected nerve cells very efficiently; various publications describe adenoviral vectors that express glial maturation factor (FR2717497), brain derived neurotropic factor (FR2717496) and acidic fibroblast growth factor (FR2717495); PCT Publication No. WO 95/26409 describes adenoviruses containing the DNA sequence for basic fibroblast growth factor to infect cells directly or via implants to treat neurological disorders; PCT Publication No. WO 96/00790 describes adenoviruses containing DNA encoding superoxide dismutase (SOD) to treat neurodegenerative diseases and excessive SOD expression; and PCT Publication No. WO 96/01902 describes adenoviruses expressing nitric oxide synthase for gene therapy where angiogenesis is required for treating disorders of the CNS.

Adenoviruses can be genetically modified to reduce the levels of viral gene transcription and expression, including adenoviruses defective in the E1 and E4 regions (PCT Publication No. WO 96/22378) and adenoviruses with an inactivated E1 region but also with altered genomic organization reducing the number of viable viral particles produced if recombination occurs with the host genome (PCT Publication No. WO 96/13596). PCT Publication No. WO 96/10088 describes defective adenoviruses with an inactivated IVa2 gene. PCT Publication No. WO 95/02697 describes an adenovirus defective in regions E1 and E2, E4, or L1–L5.

Combination virus ("plasmovirus") vectors. In another embodiment, a gene can be introduced using a combined virus, also termed plasmovirus (Genopoietic, France) vector system. Plasmovirus systems permit one cycle of infectious virus formation in infected host cells. In these systems, a complementing gene(s) for defective viral genome sequences and the defective viral sequences are both provided to target cells in vivo or in vitro. The primary infected cells produce infectious, defective virus. By permitting one cycle of infectious defective virus formation in infected cells, plasmovirus technology amplifies gene delivery in vitro and, particularly, in vivo. This cycle of infectious virus formation in situ permits wider infection of tumor cells in a tumor, thus enhancing the anti-tumor effect and reducing reliance on the bystander effect. See PCT Publication Nos. WO 95/22617, WO 95/26411, WO 96/39036, WO 97/19182.

Non-viral vectors. Alternatively, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner et. al., Proc. Natl. Acad. Sci. USA, 1987, 84:7413–7417; Felgner and Ringold, Science, 1989, 337:387–388; see Mackey et al., Proc. Natl. Acad. Sci. USA, 1988, 85:8027–8031; Ulmer et al., Science, 1993, 259:1745–1748). Useful lipid compounds and compositions for transfer of nucleic acids are described in PCT Publication Nos. WO 95/18863 and WO 96/17823, and in U.S. Pat. No. 5,459,127. Lipids may be chemically coupled to other molecules for the purpose of targeting (see Mackey et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., PCT Publication No. WO 95/21931), peptides derived from DNA binding proteins (e.g., PCT Publication No. WO 96/25508), or a cationic polymer (e.g., PCT Publication No. WO 95/21931).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., J. Biol. Chem., 1992,267:963–967; Wu and Wu, J. Biol. Chem., 1988, 263:14621–14624; Canadian Patent Application No. 2,012, 311; Williams et al., Proc. Natl. Acad. Sci. USA, 1991, 88:2726–2730). Receptor-mediated DNA delivery approaches can also be used (Curiel et al., Hum. Gene Ther., 1992, 3:147–154; Wu and Wu, J. Biol. Chem., 1987, 262: 4429–4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci., 1998, 321:893; PCT Publication Nos. WO 99/01157, WO 99/01158, and WO 99/01175).

Combination Therapies

The present invention provides for further enhancement of the anti-tumor effect by including additional anti-tumor treatments with the anti-tumor gene. For example, the present invention contemplates further combinations with tumor growth inhibitors, anti-angiogenesis treatment, tumor antigen and whole tumor vaccines, chemotherapeutic agents, radiation, and surgery (tumor resection).

Tumor growth inhibitors. The term "tumor growth inhibitor" is used herein to refer to a protein that inhibits tumor growth, such as but not limited to interferon (IFN)-γ, tumor necrosis factor (TNF)-α, TNF-β, and similar cytokines. Alternatively, a tumor growth inhibitor can be an antagonist of a tumor growth factor. Such antagonists include, but are not limited to, antagonists of tumor growth factor (TGF)-β and IL-10. The present invention contemplates administration of tumor growth inhibitor proteins systemically, or alternatively by gene therapy. In a specific gene therapy embodiment, the gene therapy vector is administered directly to the tumor.

Anti-angiogenic factors. Tumor angiogenesis is an integral part of tumor progression and a variety of therapies targeted to inhibit angiogenesis are under development as cancer therapies. Anti-angiogenesis molecules vary from anti-angiogenic proteins to small molecules that block growth factor receptor mediated effects. Anti-angiogenesis therapies primarily reverse the growth/apoptosis balance of the tumor and induce dormancy. Once the administration of these therapies is halted, angiogenesis can resume and tumor growth progresses.

An "anti-angiogenic factor" is a molecule that inhibits angiogenesis, particularly by blocking endothelial cell migration. Such factors include fragments of angiogenic proteins that are inhibitory (such as the ATF of urokinase), angiogenesis inhibitory factors, such as angiostation (O'Reilly et al., Cell, 1994, 79:315–328) and endostatin; tissue inhibition of metalloproteinase (Johnson et al., J. Cell. Physiol., 1994, 160:194–202); soluble receptors of angiogenic factors, such as the urokinase receptor or FGF/VEGF receptor (Wilhem et al., FEBS Letters, 1994, 337:131–134); molecules which block endothelial cell growth factor receptors (O'Reilly et. al., Cell, 1997, 88:277–285; O'Reilly, Nat. Med., 1996, 2:689–692), and Tie-1 or Tie-2 inhibitors. Generally, an anti-angiogenic factor for use in the invention is a protein or polypeptide, which may be encoded by a gene transfected into tumors using vectors of the invention. For example, the vectors of the invention can be used to deliver a gene encoding an anti-angiogenic protein into a tumor in accordance with the invention.

Immune activation. Administration of various immunostimulatory molecules (cytokines, lymphokines, and chemokines, for example), such as CM-CSF and IL-2, can stimulate any immune response in conjunction with the tumor suppressor activity of caspase-8. The immunostimulatory molecules can be delivered as proteins, e.g., by intravenous injection, or as therapeutic expression vectors, for expression in the host.

In order to increase the tumor antigen specific immune response, one could introduce defined tumor associated antigens (TAA) in the system to specifically increase the level of antigen. These TAA could be introduced as cells, cell extracts, proteins, or peptides, or alternatively as genes in any viral or non-viral expression vectors. Besides the defined antigen based vaccines, a number of vaccine strategies are being explored in the laboratory as well as in the clinic. One well researched strategy in animal models is the modification of autologous or allogeneic tumor cell using cytokine genes (e.g., IL-2, GM-CSF, IL-12, IL-4) as well as some key costimulatory molecule genes (e.g., B7.1, B7.2). These gene modified tumor vaccines prove the concept of breaking peripheral tolerance and anergy using immunological mechanisms (Clary et al., Cancer Gene Ther., 1997, 4:97–104; Gilboa, Semin. Oncol., 1996, 23:101–107).

Chemotherapeutic agents, radiation, and surgery (tumor resection). Although the methods of the invention are effective in inhibiting tumor growth and metastasis, the vectors and methods of the present invention are advantageously used with other treatment modalities, including without limitation surgery, radiation, chemotherapy, and other gene therapies.

For example, the vectors of the invention can be administered in combination with nitric oxide inhibitors, which have vasoconstrictive activity and reduce blood flow to the tumor.

In another embodiment, a vector of the invention can be administered with a chemotherapeutic such as, though not limited to, taxol, taxotere and other taxoids (e.g., as disclosed in U.S. Pat. Nos. 4,857,653; 4,814,470; 4,924,011, 5,290,957; 5,292,921; 5,438,072; 5,587,493; European Patent No. EP 253 738; and PCT Publication Nos. WO 91/17976, WO 93/00928, WO 93/00929, and WO 96/01815), or other chemotherapeutics, such as cis-platin (and other platinum intercalating compounds), etoposide and etoposide phosphate, bleomycin, mitomycin C, CCNU, doxorubicin, daunorubicin, idarubicin, ifosfamide, and the like.

Screening and Chemistry

Identification of the role of CASP8 in cancer provides for development of screening assays, particularly for high throughput screening of molecules that agonize or antagonize the activity of CASP8. In particular, indicator cells that are specially engineered to indicate the activity of CASP8, particularly initiation of the death process, can serve as targets to identify either a CASP8 inducer or replacement.

For example, in one embodiment, cells in which a CASP8 gene is inactivated are contacted with a candidate compound and cell apoptosis is evaluated or detected. Such an assay will identify CASP8 agonists, i.e., molecules that re-activate CASP8 expression (such as 5-aza-2'-deoxycytidine), or substitutes, i.e., that activate the death pathway in the absence of CASP8. In a preferred embodiment of the invention, cells in which CASP8 is inactivated because of methylation of the promoter are used in the assay. Candidate compounds that lead to caspase-8 expression or initiation of apoptosis are selected for their ability to overcome the promoter methylation.

In an alternative embodiment, cells that express caspase-8 (whether endogenously or by genetic engineering) are contacted with a candidate compound and cell apoptosis is evaluated or detected. Such an assay will indentify CASP8 antagonists, i.e., molecules that inhibit CASP8 activity and prevent initiation of the cell death pathway.

Accordingly, the present invention contemplates methods for identifying specific agonists and antagonists of CASP8 activity using various screening assays known in the art.

Any screening technique known in the art can be used to screen for CASP8 agonists or antagonists. The present invention contemplates screens for synthetic small molecules as well as screens for natural molecules that agonize or antagonize the activity of CASP8 in vivo. For example, natural products libraries can be screened using assays of the invention for molecules that agonize or antagonize CASP8 activity.

One approach uses recombinant bacteriophage to produce large libraries. Using the "phage method" (Scott and Smith, Science, 1990, 249:386–390; Cwirla, et al., Proc. Natl. Acad. Sci. USA, 1990, 87:6378–6382; Devlin et al., Science, 1990, 49:404–406), very large libraries can be constructed ($10^6$–$10^8$ chemical entities). A second approach uses primarily chemical methods, of which the Geysen method (Geysen et al., Molecular Immunology, 1986, 23:709–715; Geysen et al. J. Immunologic Method, 1987, 102:259–274; and the method of Fodor et al. (Science, 1991, 251:767–773) are examples. Furka et al. (14th International Congress of Biochemistry, 1988, Volume #5, Abstract FR:013; Furka, Int. J. Peptide Protein Res., 1991, 37:487–493), and U.S. Pat. Nos. 4,631,211 and 5,010,175 describe methods to produce a mixture of peptides that can be tested as agonists or antagonists.

In another aspect, synthetic libraries (Needels et al., Proc. Natl. Acad. Sci. USA, 1993, 90:10700–4; Ohlmeyer et al., Proc. Natl. Acad. Sci. USA, 1993, 90:10922–10926; PCT Publication Nos. WO 92/00252 and WO 94/28028) and the like can be used to screen for CASP8 ligands according to the present invention.

Various reporter gene assays can be used to evaluate initiation of the death-inducing signaling complex. In a specific embodiment, infra, a green fluorescent protein expression assay permits evaluation of caspase-8 activity. GFP has been modified to produce proteins that remain functional but have different fluorescent properties, including different excitation and emission spectra (U.S. Pat. No. 5,625,048 and PCT Publication No. WO 98/06737); an enzyme recognition site (PCT Publication No. WO 96/23898); increased intensity compared to the parent proteins (PCT Publication No. WO 97/11094); higher levels of expression in mammalian cells (PCT Publication No. WO 97/26633); twenty times greater fluorescence intensity than wild-type GFP(PCT Publication No. WO 97/42320); and mutants excitable with blue and white light (PCT Publication No. WO 98/21355). Other reporter genes include luciferase, β-galactosidase (β-gal or lac-Z), chloramphenicol transferase (CAT), horseradish peroxidase, and alkaline phosphatase. In addition, expression of almost any protein can be detected using a specific antibody.

Reporter gene expression can be tied to expression or activation of any component of the DISC system. In a specific example, infra, a GFP-expression vector containing the death receptor DR3 was used to evaluate caspase-8 activity. Other DISC proteins, such as the Fas receptor, FADD, FasL, FAP, FAF, Trail/DR-2, TNFRp55, TRADD, RIP, and L32 can be similarly modified. In these assays, candidate compound can be tested for their ability to inhibit apoptosis in cells that express caspase-8, or for their ability to initiate apoptosis in cells in which caspace 8 is inactivated.

EXAMPLES

The following Examples are provided to illustrate the invention without being limiting in any way.

Example 1

Structure and Chromosome Localization of the Human CASP8 Gene

This Example describes isolation of the human gene corresponding to caspase-8, CASP8, and determination of its structure and chromosomal location. The present study details this characterization, EcoRI and HindIII restriction fragment length polymorphisms (RFLPs), and demonstrates that CASP8 is localized to human chromosome 2 band q33–34, a region frequently deleted in human tumors. These results permit further study of the apoptotic signaling pathway in tumor cells.

Materials and Methods

Isolation and characterization of the human CASP8 genomic clones. Human caspase-8 cDNAs were obtained by computer analysis of a human EST library (Washington University-NCI Human EST Project). Three EST cDNAs were isolated. DNA sequencing of the caspase-8 EST DNAs was carried out as previously described using automated fluorescent-based DNA sequence analysis using Perkin Elmer/Applied Biosystems Division DNA sequencers models 373–377, with TaqFS enzyme and multiple oligonucleotide primers derived from the published cDNA sequence (Muzio et al., Cell, 1996, 85:817; Boldin et al., Cell, 1996, 85:803). Oligonucleotides were spaced approximately 80–100 bp apart spanning the cDNA. All DNA sequence data was analyzed using the IntelliGenetics program.

The human CASP8 gene was isolated from a human BAC genomic library (Genome Systems, Inc.) by hybridization with the corresponding human cDNA. Two BAC clones containing CASP8 related DNA sequences were identified (clones BAC43 and BAC 44 with the clone addresses BACH 43(K10) and BACH 44(M7); Genome Systems, Inc., St. Louis, Mo.). Their identity was confirmed by DNA sequence analysis of the entire coding region, the 3' UTR, and a portion of the 5' untranslated region (UTR). In addition, when necessary, HindIII fragments containing the entire gene were subcloned into pKS, and the resulting plasmid DNA used for double strand DNA sequence analysis. Using oligonucleotide primers designed for sequencing the cDNA clones, all exons and intron/exon boundaries were sequenced in both directions. Oligonucleotides were spaced approximately 80–100 bp apart spanning the cDNA. All DNA sequence data was analyzed using the IntelliGenetics program.

Southern and Northern blotting. Genomic DNA was isolated from cell lines as previously described (Amann et al., Genom, 1996., 32:260–265). Ten micrograms was then digested with either EcoRI or HindIII, the DNA fragments resolved by agarose gel electrophoresis in 1×TAE buffer, and the DNA transferred to Duralose membrane (Stratagene, San Diego, Calif.). These Southern blots were then hybridized with a [$^{32}$P-γ-dCTP]-labeled full length caspase-8 cDNA fragment overnight at 42° C. as described previously. The filters were then washed 3× with 2×SSC at 42° C. and 1× with 2×SSC at 68° C. and the blots visualized by exposure to Kodak XAR-5 film for six days at −80° C.

Northern blots (total human tissue, human fetal tissue, and human lymphoid tissue) were obtained from Clontech (Palo Alto, Calif.). Hybridizations and washes were performed exactly as described for Southern blotting. These Northern blots were visualized by exposure to Kodak XAR-5 film at −80° C. for four days. Equivalent levels of mRNA were confirmed by hybridization to a β-actin cDNA (data not shown).

Fluorescent in situ hybridizatioin (FISH) analysis. Bromodeoxyuridine-synchronized and phytohemagglutinin-stimulated peripheral blood lymphocytes from a normal male donor were used as the source of metaphase chromosomes for the chromosomal localization studies. Purified DNA from BAC clones containing the human CASP8 gene (CASP 43 and CASP 44) were labeled for FISH analysis by nick-translation with digoxigenin-11-UTP (Boehringer Mannheim). Slides were baked at 55° C. for one hour, RNase treated, denatured in 70% formamide/2×SSC for two minutes at 70° C., and denatured with 100% ethanol. The labeled probe was denatured and hybridized to the chromosomes overnight in the presence of 50% formamide, 10% dextran sulfate, and human COT-1 genomic DNA. Washes were performed at 46° C. To confirm the localization of the human CASP8 gene, one set of metaphase chromosomes was simultaneously hybridized with a biotin labeled genomic heterochromatin specific clone on human chromosome 2 (Oncor, Inc.) Specific hybridization signals were detected by incubating the hybridized slides in fluorescein-conjugated sheep antibodies to digoxigenin (Boehringer Mannheim). Two color specific probe signals were detected by incubating the hybridized slides in fluorescein-conjugated sheep antibodies to digoxigenin and Texas red Avidin (Vector Labs). All of the mitotic figures examined placed CASP8 at 2q33–34 (FIG. 3); band assignment was determined by measurement of twenty chromosomes 2.

Results and Discussion

Structure of the human CASP8 gene. Southern hybridization of human genomic DNA with the caspase-8 cDNA probe yields a pattern consistent with a single-copy gene contained within both BAC clones (data not shown). CASP8 contains 10 exons spanning ~30 kb as shown in FIG. 1 (GenBank accession numbers for CASP8 sequences are: AF102139–102146). The 5' UTR is contained in three exons, while the 3' UTR is encoded by one exon. The open reading frame (ORF) begins in exon 3 (FIG. 1A). Sequences of exons 3, 4, 5, 6, 7, 8, 9, and 10, including partial sequences of the flanking introns, were determined. These sequences are depicted in SEQ ID NOS:3–10, respectively. All of the exon/intron splice junction regions, as well as the exons themselves, were analyzed (Table 1). (The boundaries in Table 1 permit identification of the coding and non-coding parts of the genomic sequences of SEQ ID NOS:3–110, and thus deduction of the amino acid sequence of the polypeptide segment encoded by each exon.) In each instance but one (i.e., splice acceptor site of intron 4/exon5), the donor and acceptor splice junction sequences conform to the GT/AG rule (Breathnach et al., Ann. Rev. Biochem., 1981, 50:349–383). One of the DEDs is contained entirely in exon 3, while the second DED is contained in exons 4 and 5. The linker region of caspase-8, located between the DEDs and the cysteine protease domain, is encoded by exons 6–8. All of these exons are relatively small in size, ranging from 45–142 bp (FIG. 1). Exons 9–10 contain the large and small subunits that constitute the cysteine protease catalytic domain. Much of this cysteine protease domain, including the catalytic cysteine residue (QACXG) (SEQ ID NO:11) of the large subunit and the substrate specificity determinants of the small subunit (RNPAEGTW) (SEQ ID NO:12), are found in exon 9.

Northern blot analysis of human adult tissues demonstrated that caspase-8 mRNA is expressed fairly ubiquitously (data not shown). Testis, skeletal muscle and kidney express very little caspase-8, while brain appears to express

TABLE 1

Exon/Intron Boundaries of the Human CASP8 Gene ORF.

| Exon | Exon/Intron Sequence | SEQ ID NO | Intron | Exon/Intron Sequence | SEQ ID NO | Exon |
|---|---|---|---|---|---|---|
| 2 | ... GGTGGAGCGGgtgtgggtcg ... | 13 | 2 | ... tattttgacttagATTATATTCT ... | 14 | 3 |
| 3 | ... GCC TAC Aggtgggtggaaactc ... | 15 | 3 | ... cccaaccacaaagG GTC ATG ... | 16 | 4 |
| 4 | ... GAT GAC ATGgtgcctgggaac ... | 17 | 4 | ... ttctcctcctcttacAAC CTG ... | 18 | 5 |
| 5 | ... TTC AGC AAAgtaccgcaatttc ... | 19 | 5 | ... tttgccttatctgagGAG AGA ... | 20 | 6 |
| 6 | ... TCA AAT gttagttaatttactat ... | 21 | 6 | ... tcccgggttttcccgagGGG GAG ... | 22 | 7 |
| 7 | ... TCA CAGgtagcacggaaaacc ... | 23 | 7 | ... gggttttgtaatccagACT TTG ... | 24 | 8 |
| 8 | ... GAT GCA Ggtgggcggggctc ... | 25 | 8 | ... agtttcacttttcagGG GCT TTG ... | 26 | 9 |
| 9 | ... TGT CCT Cggtaagttttgcctact ... | 27 | 9 | ... gtgaatagtttgcagA GGC GAT ... | 28 | 10 |

Notes to Table 1: Upper case letters correspond to the ORF; lower case letters to intronic sequences. The triplet codons are shown for the ORF at the exon/intron boundaries. All splice donor and acceptor sites fit the consensus sequence, except for the one in bold and underlined.

The structure of the human CASP8 gene is identical to the mouse with regard to the exon/intron organization and exon size (Sakamaki et al., Eur. J. Biochem., 1998, 253:399–405). The sequence of the exon/intron boundaries is shown in Table 1. The structure of the mouse gene, corresponding to the ORF portion of the mRNA, is encoded by eight exons. This is identical to the eight exons (i.e., exons 3–10) that encode the human ORF. However, the 5' UTR of the mouse gene was not analyzed (Sakamaki et al., 1998, supra). A similar exon/intron organization, with respect to the structural domains of the corresponding protein, has also been described for a close relative of CASP8, CASP10 (Rasper et al., Cell Death & Diff., 1998, 5:271–288). At least eight different isoforms of caspase-8, all generated by alternative splicing, have been reported (Boldin et al., 1996, supra). We can confirm that the transcripts are, indeed, alternatively spliced products generated from the CASP8 gene that correspond to specific exons (FIG. 1). The function of several of these alternatively spliced caspase-8 products is currently unknown, but others have reported that only two of these isoforms are found in much abundance in the human cell lines they examined (Scaffidi et al., J. Biol. Chem., 1997, 272:26953). Finally, BAC 43 and BAC 44 also contain the CASPIO gene, as confirmed by both PCR and limited DNA sequence analysis of the first and last exons of the gene (FIG. 1). The CASP10 gene is located ~20–30 kb 5' of the CASP8 gene in the same transcriptional orientation.

Southern and Northern blot analysis of CASP8, and two RFLPs associated with the gene. Southern blot analysis of total genomic DNA from three different human neuroblastoma cell lines was performed to determine whether restriction fragment length polymorphisms are associated with CASP8 (FIG. 2). Two different restriction enzymes, EcoRI and HindIII, were associated with RFLPs in CASP8. The EcoRI polymorphism involved a 4.7 kb band that increased to about 8.0 kb (FIG. 2A, NB5). Interestingly, the same cell line also had a HindIII RFLP involving a 4.0 kb band that increased in size to ~7.2 kb (FIG. 2B, NB5). These RFLPs can now be used to track specific alleles associated with CASP8 in families and/or individuals with different genetic diseases/cancer to determine whether this gene is a candidate for mutation.

extremely high levels of this mRNA. This is in agreement with previously reported results for the tissue distribution of caspase-8 mRNA (Boldin et al., 1996, supra). Of some interest is the expression of this gene in human lymphoid tissues, including spleen, lymph node, thymus, peripheral blood leukocytes (PBLs), bone marrow, and fetal liver, particularly those that undergo significant apoptosis. Northern blot analysis of these tissues shows that caspase-8 is expressed (data not shown). The highest level of expression was found in PBLs, consistent with caspase-8's role in the death of peripheral T cells. Lymph node and spleen also expressed significant levels of caspase-8 mRNA, while thymus, bone marrow, and fetal liver expressed very low levels.

CASP8 mRNA expression was also evaluated in fetal tissues (embryonic RNAs, in addition to liver). While human fetal brain expressed undetectable levels of caspase-8 mRNA, and human fetal liver and lung expressed low levels of caspase-8 mRNA, human fetal kidney expressed the highest level of caspase-8 mRNA (data not shown), similar to what has been reported during the mouse development (Varfolomeev et al., Immunity, 1998, 9:267–276).

Figure 3A:
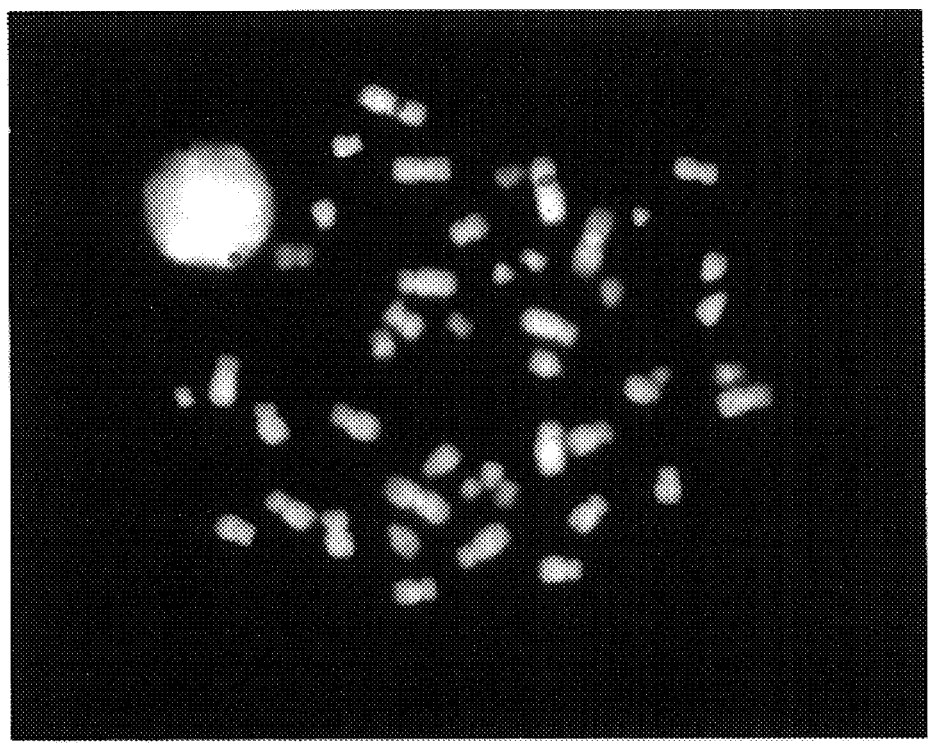
FIGS. 3A, 3B, 3C, and 3D. Fluorescent in situ hybridization (FISH) localization of the human BAC clone containing CASP8. A: FISH on metaphase chromosome spreads with the human genomic BAC clone CASP8.43 labeled with digoxigenin-11-UTP which is visualized with fluorescein-conjugated avidin (green; denoted by the arrows), and the human genomic chromosome 2 centromeric probe labeled with biotin-14-dATP which is visualized with Texas red Avidin (red; denoted by the arrowheads) (color photograph). For comparison, the chromosomes were visualized with DAPI counter staining. An interphase nucleus is also shown to demonstrate that the gene is single copy. B: Ideogram of G-banded human chromosome 2 indicating the location of CASP8 (2q33–34). C, D: Fiber FISH analysis of the deletion in one of the NB7 alleles (C) and in the EBV-transformed B-cell containing a normal CASP8 allele (D). A P1 clone containing only CASP10 (green) was used as a reference for measurements to compare the length of the CASP8 P1 hybridization signal (red) from NB7 with a EBV-transformed B-cell (the CASP8 P1 does not contain CASP10). The approximate size of the deletion is indicated.
Figure 3C:
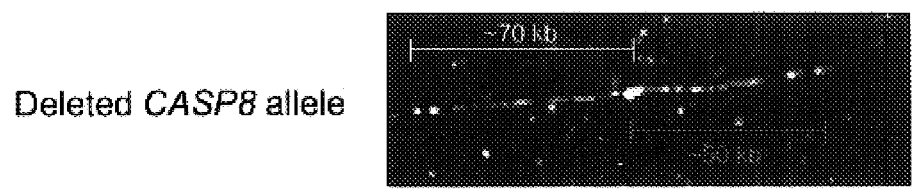
Figure 3D:
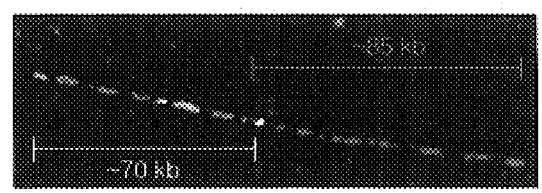
Figure 3B:
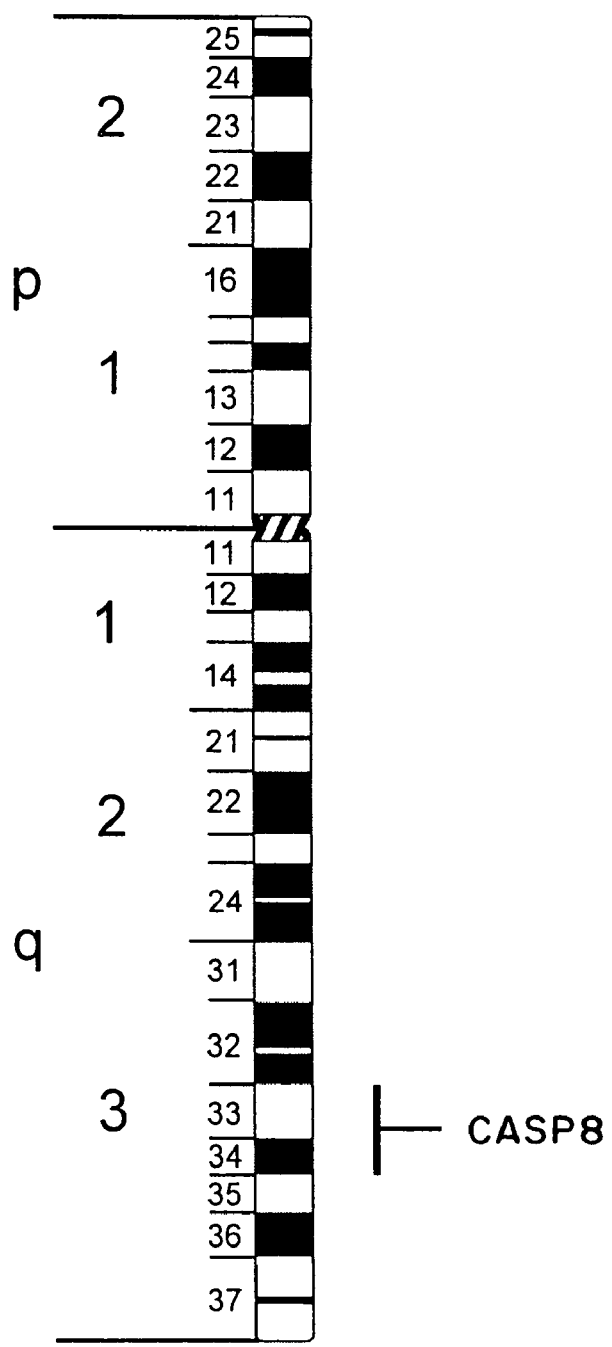

Chromosome localization of the human CASP8 gene. By fluorescent in situ hybridization (FISH) analysis, the CASP8 gene is localized to human chromosome band 2q33–34 (FIGS. 3A and 3B). This assignment was confirmed by somatic cell hybrid analysis (data not shown) and it is consistent with the report of another group. While this research was in progress Rasper et al., supra, reported that they had identified the 5' UTR of CASP8 in a genomic PAC clone containing the CASP10 and USURPIN genes, and that this PAC localized to 2q33–34. This is also the chromosome region the human CASPIO gene was localized to by Fernandes-Alnemri et al., Proc. Natl. Acad. Sci. USA, 1996, 93:7464–7469, suggesting that all of these genes may have arisen by tandem duplications. Analysis of our BAC clones indicates that CASP10 is approximately 30 kb form the 5' end of CASP8. Tandem duplication of other caspases, e.g., CASP1, CASP4, and CASP5 at 11q22.2–22.3 (Nasir et al., Mam. Genome, 1997, 8:611–613), as well as several functional death receptors and their decoys, e.g., DR4, DR5, DcR1, and DcR2 at 8p21 (Golstein, 1997, Curr. Biol, 7:R750–753), have been observed.

Human gene duplications of this type have been associated with other chromosome regions that are altered during tumorigenesis (Baens et al., Genom., 1995, 29:44–52). Such duplications may reflect the relative instability of these chromosomal DNA regions (Baens et al., 1995, supra). In fact, current physical and genetic mapping have demonstrated that this region of chromosome 2 is frequently involved in tumorigenesis. Several studies have shown that there is frequent loss of heterozygosity (LOH) and the 2q33 region in a number of human tumors, including small-cell lung carcinoma, non-small-cell lung carcinoma, colorectal carcinoma, neuroblastoma and uterine cervical carcinoma (Kohno et al., Oncology, 1994, 9:103—103; Takita et al., Oncology, 1995, 11:1829–1834). This has led to speculation that a tumor suppressor gene is located in this region of chromosome 2 (Kohno et al., 1994, supra). The data in Example 2 unexpectedly indicate that CASP8 is such a tumor suppressor, which is consistent with its function as an effector of apoptotic signaling pathways. The identification of EcoRI and HindIII RFLPs should facilitate this type of analysis.

Additional studies, shown in Example 2, have established that abnormalities in the structure and/or regulation of CASP8 occur in specific tumors. Recently, Evan and colleagues (Heuber et al., Science, 1997, 278:1305–1309) demonstrated that the apoptosis associated with c-myc overexpression was mediated by the Fas pathway. The authors proposed that, given their role in apoptotic signaling, aberrant regulation of one or more of the genes corresponding to components of this pathway may be observed in certain transformed cells, particularly those with elevated levels of myc oncoproteins. It is only now that the structure and localization of CASP8 is known that it is possible to examine these types of tumors to determine aberrant expression of caspase-8.

Example 2

CASP8 Inactivation in Human Neuroblastoma and Small Cell Lung Carcinoma

Materials and Methods

Materials and methods for this Example are substantially the same as those described in Example 1.

Neuroblastoma cell lines NB 1–8, NB10, and NB12–21 from St. Jude Children's Research Hospital were tested. In addition, Memorial Sloan Kettering neuroblastoma cell lines SK-N-AS, SK-N-F1, and SK-N-DZ, and NIH small-cell lung carcinoma cell lines NCIH 889, NCIH 810, NCIH H69, HCIH H82, and NCIH N417 were analyzed. HeLa and Jurkat lines were used as controls.

Results

Southern blot and FISH analysis of genomic DNA from neuroblastoma cell lines. Blots with genomic DNA from the NB cell lines were hybridized with the caspase-8 cDNA and with a caspase-10 cDNA. It was found that with line NB7, there is no hybridization signal with the caspase-8 probe, but the caspase-10 probe detected its corresponding gene. The CASP1O gene is about 30 kb from the 5' end of CASP8 (Example 1). Therefore, Southern analysis demonstrates that CASP8 is homozygously deleted from NB7 (indicated by –/–).

Figure 4A:
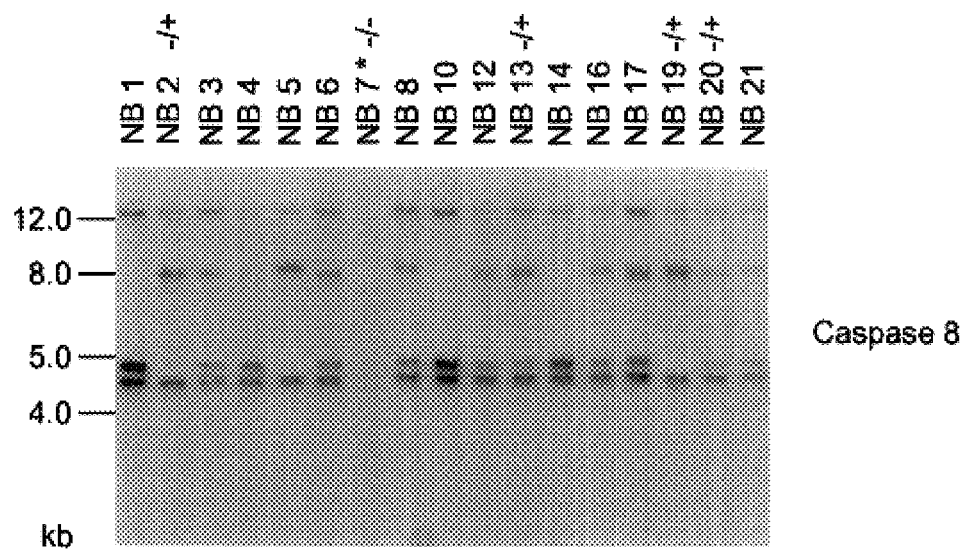
FIGS. 4A, 4B, 4C, 4D, and 4E. Analysis of CASP8 structure and expression in human neuroblastoma cell lines. Heterozygous (+/−) deletions determined by FISH are indicated above the appropriate cell line. A: Southern blot analysis of the human CASP8 locus. The variant 8.0 and 4.8 kb EcoRI fragments of CASP8 are polymorphisms. B: Southern blot analysis of the human CASP10 locus in the same NB cell lines. C:Northern blot analysis of caspase-8 mRNA expression in the same NB cell lines. D:Western blot analysis of the caspase-8 and caspase-10 proteins in the various neuroblastoma cell lines from SJCRH (NB1–NB21), Memorial Sloan Kettering (SK), and small-cell lung carcinoma cell lines (NC1H). The blot includes tubulin control for the protein loading quantification. E:Immunoblot analysis of N-Myc expression in the NB cell lines.
Figure 4B:
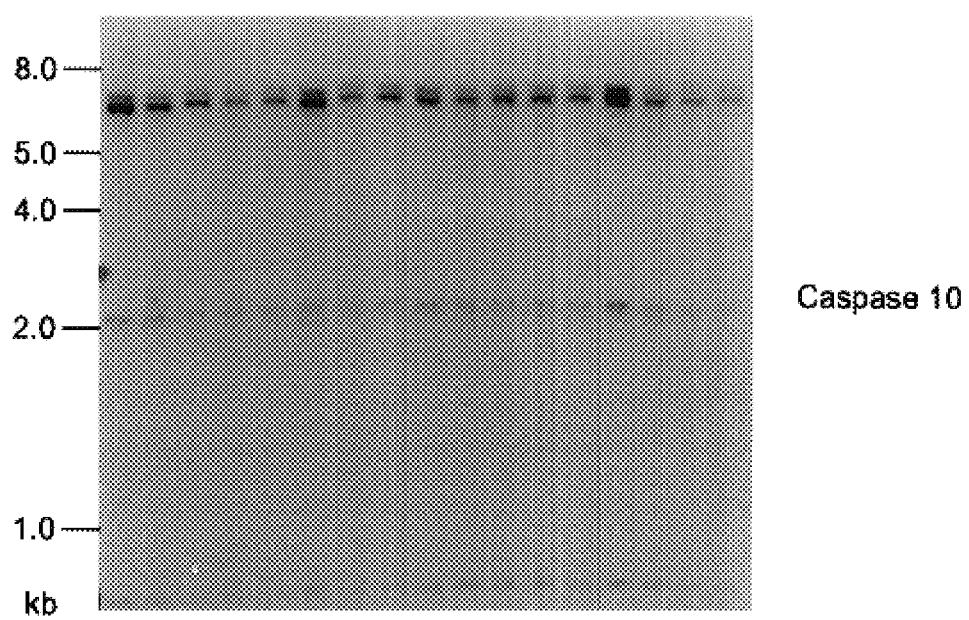

As all other neuroblastoma cell lines tested by Southern analysis were positive for CASP8 genomic DNA (FIGS. 4A and 4B), we decided to investigate whether some of these cell lines contained hemizygous deletions of CASP8. Indeed, when fluorescent in situ hybridization (FISH) analysis with the human CASP8 BAC genomic clone was used to determine whether the ~150 kb encompassed by this clone, containing the entire CASP8 gene, was deleted from the cells, it revealed allelic loss in five of the eighteen NB cell lines examined (Table 2, indicated by +/–). In one example with the NB20 cell line, three chromosomes-2 contained CASP8 signals, while three others did not. The ratio of chromosomes-2 with CASP8 signals to chromosomes-2 without CASP8 signals for other cell lines was 18% (NB-2), 78% (NB-13), 75% (NB-15), and 68% (NB-19), respectively.

The small size of the 2q33 deletions in NB7 did not allow their detection by conventional FISH using the BAC clone. Fiber FISH analysis of NB7 with smaller P1 phage clones, containing either CASP8 or CASP10, demonstrated that one allele was missing much of CASP10 and CASP8, while the other allele had an ~20–35 kb deletion encompassing the immediate CASP8 region and did not affect CASP1O (FIGS. 3C and 3D).

Figure 4C:
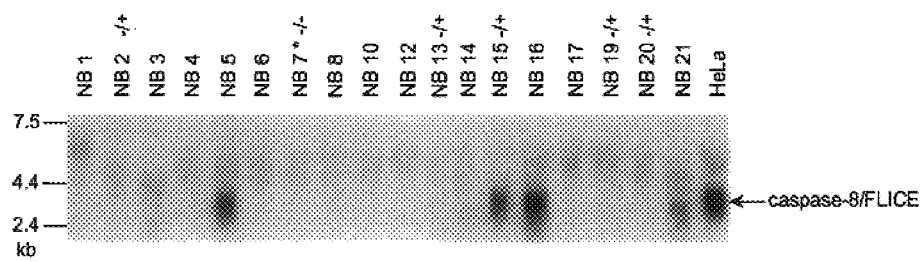
Figure 5:
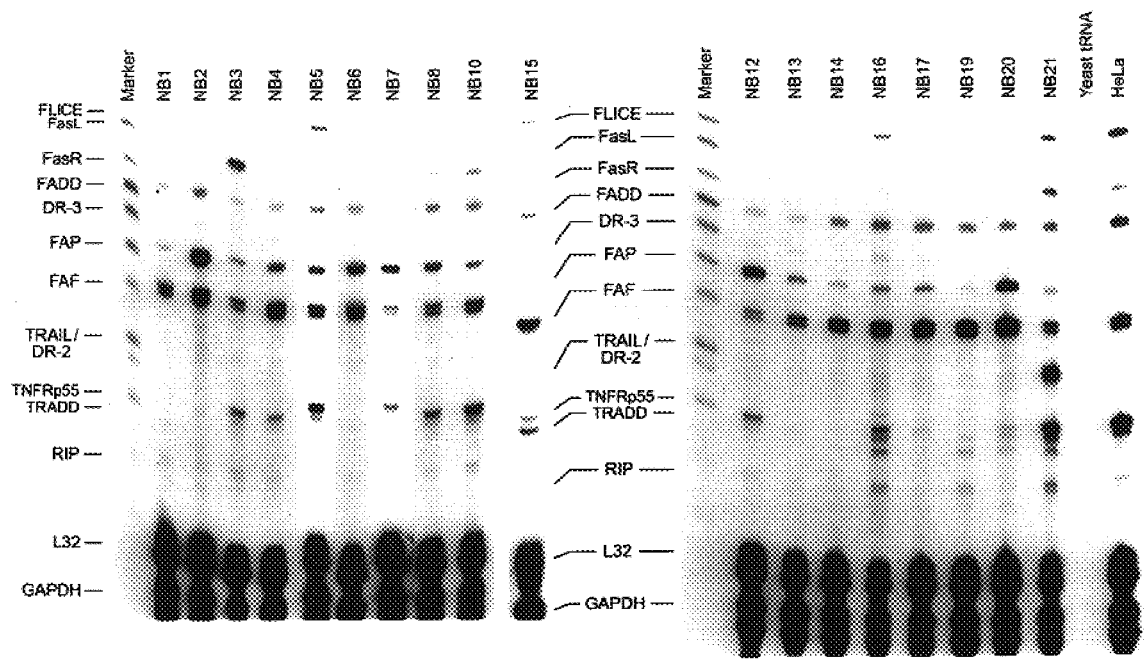
FIG. 5. RNase protection analysis of the expression of apoptotic genes in human neuroblastoma cell lines.

Northern blot analysis of RNA from the neuroblastoma cell lines. Northern analysis indicated that the approximately 3.0 kb CASP8 mRNA is present in only NB5, NB15, NB16, and NB21 (as well as the control HeLa cell line) (FIG. 4C). These data coincide with the RNase protection data, except that the more sensitive RNase protection analysis demonstrated that NB3 cells also express very low levels of CASP8 mRNA (FIG. 5 and discussed below).

Figure 4E:
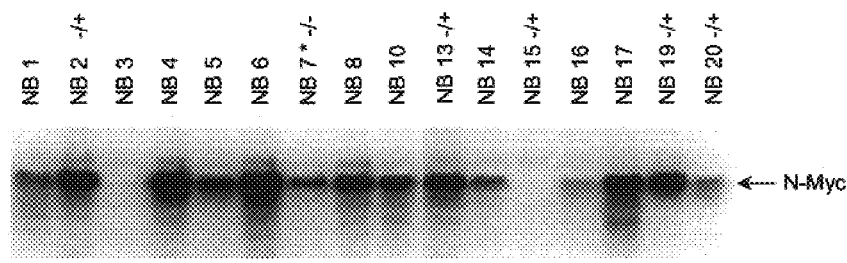
Figure 4D:
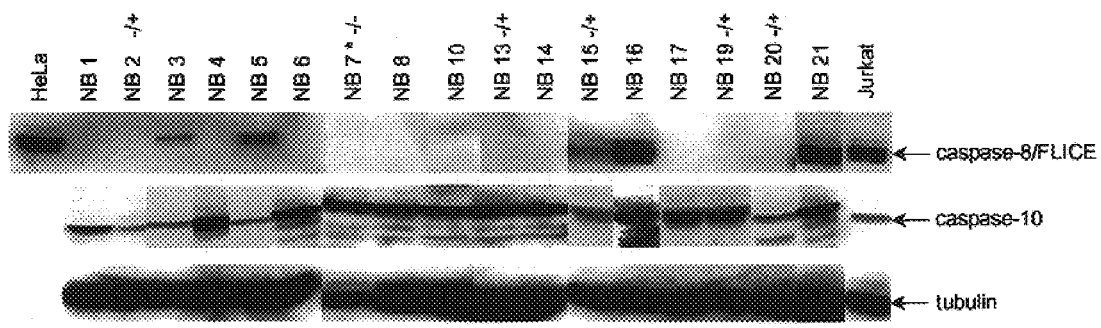

Western blot analysis of the caspase-8 protein in the various neuroblastoma cell lines from SJCRH (NB1–NB21) and Memorial Sloan Kettering (SK), and small-cell lung carcinoma cell lines (NC1H). Examination of caspase-8 expression by immunoblot analysis demonstrated that the protein was undetectable in cell lines lacking detectable mRNA (FIG. 4D). Thus, the caspase-8 protein was detected only in NB3, NB5, NB 15, NB 16, and NB21 (HeLa and Jurkat served as positive controls). In addition, only one of the SK cell lines (SK-N-AS) and two of the NCIH small-cell lung carcinoma lines (NCIH 889 and NCIH 810) express caspase-8 protein (FIG. 4D). Furthermore, amplification and expression of MYCN was highly correlated with the loss of CASP8 expression (FIG. 4E and Table 2). By contrast, caspase-10 was detected in each of the NB cell lines, indicating that alterations selectively affect caspase-8 expression.

TABLE 2

Analysis of CASP8 in human neuroblastoma cell lines

| Cell Line | CASP8 (FISH) | Casp8 mRNA | Casp8 Protein | CASP8 Methylation | CASP8 Mutation | Casp10 Protein | FasR Protein | DR3[1] Protein | Fas mAb-Apoptosis | MYCN Protein | MYCN[2] |
|---|---|---|---|---|---|---|---|---|---|---|---|
| NB1 | +/+ | — | N | Y | N | Y | N | Y | N | Low | 2–6 |
| NB2 | +/– | — | N | Y | N | Y | Y | Y | N | High | >20 |
| NB3 | +/+ | +/– | Y | N | N | Y | Y | N | Y | No | 2 |
| NB4 | +/+ | — | N | Y | N | Y | N | Y | N | High | >20 |

TABLE 2-continued

Analysis of CASP8 in human neuroblastoma cell lines

| Cell Line | CASP8 (FISH) | Casp8 mRNA | Casp8 Protein | CASP8 Methylation | CASP8 Mutation | Casp10 Protein | FasR Protein | DR3[1] Protein | Fas mAb-Apoptosis | MYCN Protein | MYCN[2] |
|---|---|---|---|---|---|---|---|---|---|---|---|
| NB5 | +/+ | + | Y | N | N | Y | N | Y | Y | Mod | 2–5 |
| NB6 | +/+ | — | N | Y | N | Y | N | Y | N | High | >20 |
| NB7 | −/−[(3)] | — | N | N | N | Y | N | Y | N | Mod | >20 |
| NB8 | +/+ | — | N | Y | N | Y | Y | N | N | High | >20 |
| NB10 | +/+ | — | N | Y | N | Y | Y | N | N | High | >20 |
| NB12 | +/+ | — | N | Y | N | Y | N | Y | N | High | >20 |
| NB13 | +/− | — | N | Y | N | Y | N | Y | N | High | >20 |
| NB14 | +/+ | — | N | Y | N | Y | N | Y | N | Low | >20 |
| NB15 | +/− | + | Y | N | N | Y | N | Y | N | No | >20 |
| NB16 | +/+ | + | Y | N | N | Y | Y | Y | Y | V. Low | 2–4 |
| NB17 | +/+ | — | N | Y | N | Y | N | Y | N | Mod | >20 |
| NB19 | +/− | — | N | Y | N | Y | Y | Y | N | High | >20 |
| NB20 | +/− | — | N | Y | N | Y | Y | Y | N | Low | >20 |
| NB21 | +/+ | + | Y | N | N | Y | Y | N | Y | Low | 2–6 |
| HeLa | +/+ | + | Y | N | N | Y | N | N | N | ND | ND |

[1]From Grenet et al., Genomics, 1998, 49: 385–393.
[2]From Beltinger et al., Cancer Res., 1995, 55: 2053–2055, and references therein.
[3]Both CASP8 alleles have been deleted in this cell line as determined by Southern blotting.

RNase protection analysis of mRNAs from the various neuroblastoma cell lines. RNA from each of the indicated neuroblastoma cell lines was examined for the expression of various cell death components: FasL, FasR, FADD, DR-3, FAP, FAF, TRAIL/DR-2, TNFRp55, TRADD, RIP, L32, and GAPDH (FIG. 5). As was found with the Northern and Western blot analyses, only NB3, NB5, NB15, NB16, and NB21 express detectable caspase-8 mRNA. All of the other essential death components are expressed in every cell line.

Discussion

These data show that inactivation of caspase-8, whether by gene deletion, mutation, or supression of expression, associates with cancer, and particularly with neuroblastoma. Thus, diagnosis and prognosis of cancer, especially neuroblastoma, can be based on the level or absence of caspase-8 expression.

These data establish an important role for caspase-8 in tumor suppression. Work with p53 and other tumor suppressor genes has established a role for gene therapy in treating various cancers. Caspase-8 is also indicated as a therapeutic tumor suppressor gene. Vectors for expression of caspase-8 will be useful in tumor cells in which caspase-8 has been inactivated. In addition, overexpression of caspase-8 in other tumor cells is expected to induce apoptosis and cell death.

Example 3

Investigation of Silencing of CASP8 by Methylation Using Methylation-Sensitive PCR Analysis. Study of Association Between CASP8 Methylation and MYCN Gene Amplification in Neuroblastoma Patient Samples and Cell Lines Materials and Methods Bisulfite treatment. Five micrograms each of EcoRI-digested DNA from cultured cells was denatured with 1/10 volume of 3M NaOH at 37° C. for 15 min. A freshly prepared solution (1.2 ml) containing sodium metabisulfite (2.5M, pH 5.0) and hydroquinone (100 mM) was added to the denatured DNA and incubated at 55° C. for 6 hrs. The bisulfite salts were removed by a Wizard desalting column (Promega, Madison, Wis.) according to the manufacturer's specifications. DNA in 100 microliters was desulphonated by addition of 1/10 volume of freshly prepared 3M NaOH and incubation at 37° C. for 15 min, before neutralizing with 166 microliters of ammonium acetate (pH 7.0) and precipitating with 2.5 volumes of ethanol. Bisulfite modified DNA was resuspended in 40 microliters of water.

PCR amplification and Primers. Amplification of the 5' untranslated region of Casp8 gene was performed in 50 microliters reaction mixtures containing 5 microliters of bisulfite treated DNA, dNTPs, each at 1.25 mM, 300 ng of each primer, 1×PCR buffer (Promega, Madison, Wis.) plus 6.7 mM $MgCl_2$ and 2.5 units of AmpliTaq polymerase (Promega).

Primer sets were designed to produce a 320 bp fragment in the upstream region of Casp8 gene extending from +221 to +541. Wild type primers were used to amplify the corresponding region from 100 ng of untreated genomic DNA. Controls without DNA were performed for each set of PCR primers. DNA not treated with bisulfite (unmodified) failed to amplify with either set of methylated or unmethylated specific primers, but readily amplified with the wild type primers—primers specific for the sequence before modification. Primers for methylated-specific bisulfite treated DNA were:

1) Sense 5' TAGGGGATTCGGAGATTGCGA 3' (SEQ ID NO:29)
2) Antisense 5'CGTATATCTACATTCGAAACGA 3' (SEQ ID NO:30) Primers for unmethylated-specific bisulfite treated DNA were:
1) Sense 5' TAGGGGATTTGGAGATTGTGA 3' (SEQ ID NO:31)
2) Antisense 5'CCATATATATCTACATTCAAAACAA 3' (SEQ ID NO:32) Primers for amplifying the corresponding wild type DNA (untreated with bisulfite) were:
1) Sense 5' TAGGGGACTCGGAGACTGCGA 3' (SEQ ID NO:33)
2) Antisense 5'CGTGTATCTGCATTCGAGGCG 3' (SEQ ID NO:34)

Reactions were hot-started at 95° C. for 5 min before the addition of AmpliTaq polymerase. Amplification was done under the following conditions: 35 cycles of 95° C. for 30 sec, 58 c for the unmethylated primers and for the wild-type primers, or 64° C. for the methylated primers, for 30 sec, and 72° C. for 45 sec for all primers. These cycles were followed by 1 cycle of extension at 72° C. for 10 min. Amplification products (10 microliters) were loaded on a 2% agarose gel in TBE buffer, stained with ethidium bromide, and directly visualized under UV illumination.

Results and Discussion

Caspase-8 western blot analysis of cell lysates from the NB8, NB10, and NB14 cell lines with (+) or without (−) 5-aza-2'-deoxycytidine. Surprisingly, other than the CASP8 deletions, we found no evidence of mutations within CASP8 coding regions in the NB cell lines (data not shown). We therefore examined DNA methylation of CASP8 regulatory sequences as an alternative mechanism through which expression could be silenced, as documented for several tumor suppressor genes, such as INK4a, CDKN1, CDKN2, PTEN, MLH1, von Hippel-Lindau, and E-cadherin (Baylin et al., Adv. Cancer Res., 1998, 72:141–196; Belinsky et al., Proc. Natl. Acad. Sci. USA, 1998, 95:11891; Whang et al., Proc.Natl.Acad.Sci.USA,1998, 95:5246–5250; Merlo et al., Nature Medicine, 1995, 1:686–692).

The role of methylation of CASP8 regulatory sequences was tested by treating NB cells with 5-aza-cytidine, a compound that promotes the demethylation of CpG dinucleotides (Merlo et al., Nature Medicine, 1995, 1:686–692). When cells were treated with 10–50 μM 5-aza-cytidine for 2–3 days, caspase-8 expression was activated in the NB8 and NB11 cell lines, but not NB14 (FIG. 6A). The NB8 and NB10, but not NB14, cells then underwent spontaneous apoptosis, presumably due to the effect of caspase-8 in the presence of elevated N-myc levels (related to MYCN gene amplification).

The data show that a number of the neuroblastoma cell lines, in addition to having deletions, have turned off the expression of caspase-8 from the remaining allele by methylation of the promoter region. This seems to be a very common mechanism for extinguishing expression of the protein. This is also the reason the DNA sequence of the promoter region(s) is extremely important.

Investigation of CASP8 promoter methylation using methylation-sensitive PCR analysis. To test for methylation directly, a CpG-rich region of the CASP8 5' flanking region was chosen for the design of oligonucleotide primers for methylation sensitive-PCR analysis. In this assay, unmethylated cytosines, but not the methylated cytosines in CpG dinucleotides, are converted to uracils after sodium bisulfite treatment of genomic DNA (Herman et al., Proc.Natl.Acad.Sci.USA, 1996, 93:9821–9826). Two separate pairs of oligonucleotide primers (21–23-mers) were designed. One primer set contained adenines substituted for each guanine in the antisense-strand, such that these primers only bind to bisulfite-modified DNA sequence corresponding to unmethylated DNA (SEQ ID NOS: 31, 32). The other primer set retained guanines at positions corresponding to cytosines in CpG dinucleotide sequences specific for methylated genomic DNA (SEQ ID NOS: 29, 30), since these residues are protected from bisulfite modification by methylation (FIG. 6B). Using primers 31 and 32 for a PCR with bisulfite-treated genomic DNA from the NB cell lines as template, the 322-bp CASP8 product was observed in NB3, NB5, NB15, NB16, and NB21, which express caspase-8, as well as the Jurkat and HeLa positive controls (FIG. 6B). DNA sequence analysis of this product from NB 16 revealed that all of the sense-strand cytosines within the 322-bp region were replaced with thymidine. When the same bisulfite-treated template DNA was used with the primers 29 and 30 a 321-bp PCR product was observed only in the NB cell lines that lacked caspase-8 expression, and in the NB3 that expresses caspase-8 at a low level (FIG. 6B). DNA sequence analysis of the 321-bp product demonstrated that only sense-strand cytosines, that are not associated with a CpG dinucleotide, were replaced with thymidine. NB cell lines with two intact CASP8 genes (e.g., NB1, NB8, NB 10) also showed evidence of no caspase-8 expression, indicating that both CASP8 alleles were silenced by methylation. Interestingly, the NB cell lines continue to express caspase-10 from a closely linked gene (FIG. 4D), arguing against global CpG dinucleotide methylation across this region of chromosome 2 band q33.

Figure 7A:
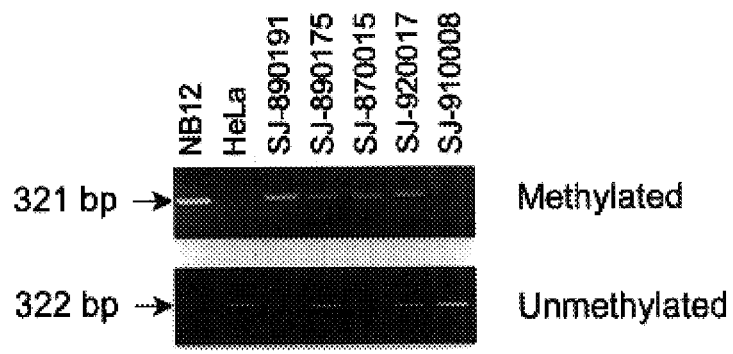
FIGS. 7A, 7B, and 7C. Analysis of neuroblastoma patient material by methylation PCR and FISH. A:Patient samples SJ-890191 and SJ-870015 generate a PCR product corresponding to methylated CASP8 alleles and little if any product using the unmethylated oligonucleotide set. Conversely, SJ-910008 generates a PCR product corresponding to unmethylated CASP8 alleles and little if any PCR product corresponding to methylated alleles. The other NB patient samples, SJ-890175 and SJ-920017, appear to contain both methylated and unmethylated CASP8 alleles. The NB12 (positive for methylated CASP8 alleles, negative for unmethylated alleles) and HeLa (positive for unmethylated CASP8 alleles, negative for methylated alleles) were used as controls. B, C:Semi-quantitative PCR analysis of SJ-910008 and SJ-890191 patient material for caspase-8 (B) and caspase-9 (C) mRNAs. The presence (+) or absence (−) of reverse transcriptase in the respective reactions is shown above each gel.
Figure 7B:
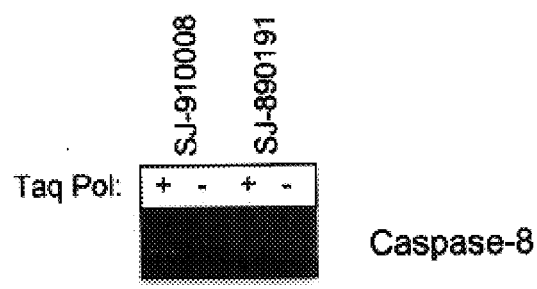
Figure 7C:
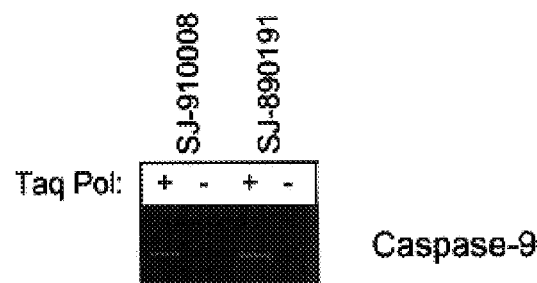

Cryopreserved primary neuroblastoma samples were examined to determine whether somatic cell loss of caspase-8 expression occurs in the tumor in vivo prior to tissue culture. A total of 42 samples were examined. In 11 of the 42 total samples analyzed, complete methylation of all CASP8 alleles was observed. Representative examples are shown in FIG. 7A. The PCR products of two patient samples correspond almost exclusively to methylated CASP8 alleles (i.e., SJ-890191 and SJ-870015). In contrast, a PCR product corresponding predominantly to the unmethylated allele was detected in one of five patient samples, while the remaining two patient samples contained PCR products in reactions amplified with both primer sets. The results listed in Table 3 for all of the remaining NB patient samples were scored in an identical manner. Semi-quantitative PCR was performed to determine whether these patient tumor cells expressed caspase-8 mRNA. For example, SJ-890191, as well as other patient samples with predominantly methylated CASP8 alleles, did not express caspase-8 mRNA, whereas SJ-910008, and other patient samples with predominantly unmethylated, or a mixture of unmethylated and methylated, CASP8 alleles, did express caspase-8 mRNA (FIGS. 7B and 7C).

TABLE 3

Analysis of Neuroblastoma Patient Tumors

| Patient Sample | Stage | Methylated CASP8 DNA | Unmethylated CASP8 DNA | CASP8 Deletion | MYCN Amplification |
|---|---|---|---|---|---|
| SJNB-920018 | 3 | − | + | N | N |
| SJNB-910008 | 1 | − | + | N | N |
| SJNB-890191 | 4 | + | − | Y | Y |
| SJNB-910007 | 4 | − | + | N | N |
| SJNB-930100 | 3 | + | + | N | Y |
| SJNB-890175 | 3 | + | + | N | Y |
| SJNB-870015 | N/A | + | − | N | Y |

TABLE 3-continued

Analysis of Neuroblastoma Patient Tumors

| Patient Sample | Stage | Methylated CASP8 DNA | Unmethylated CASP8 DNA | CASP8 Deletion | MYCN Amplification |
|---|---|---|---|---|---|
| SJNB-920017 | N/A | + | + | N | N |
| SJNB-840065 | 1 | − | + | N | N |
| SJNB-900106 | 4 | + | − | N | Y |
| SJNB-970009 | 4 | − | + | N | N |
| SJNB-960103 | 4 | + | − | N | Y |
| SJNB-960051 | 1 | + | + | N | N |
| SJNB-840089 | N/A | − | + | N | N |
| SJNB-920063 | 3 | − | + | N | N |
| POG-103 | 2 | + | + | N | N |
| POG-158 | 2 | − | + | N | N |
| POG-253 | 1 | − | + | N | N |
| POG-429 | 3 | + | + | N | N |
| POG-687 | 4 | − | + | N | N |
| POG-770 | 4 | + | + | N | N |
| POG-783 | 3 | + | + | N | N |
| POG-840 | 4 | + | − | N | Y |
| POG-1315 | 4 | + | + | N | N |
| POG-1343 | 1 | + | + | N | N |
| POG-1368 | 3 | + | + | N | N |
| POG-1418 | 2 | + | + | N | N |
| POG-1422 | 3 | − | + | N | N |
| POG-1613 | 1 | + | + | N | N |
| POG-2025 | 4S | − | + | N | N |
| POG-3087 | 4S | + | + | N | N |
| POG-3169 | 4 | − | + | N | N |
| POG-4098 | 3 | + | + | N | Y |
| POG-4177 | 4 | − | + | N | Y |
| POG-4212 | 3 | − | + | N | Y |
| POG-4316 | 4 | + | − | N | Y |
| POG-4489 | 4 | − | + | N | Y |
| POG-4499 | 4 | + | − | N | Y |
| POG-4903 | 4 | + | − | N | Y |
| POG-4911 | 4 | + | − | N | Y |
| POG-5044 | 4 | + | + | N | N |
| POG-5217 | 2 | + | − | N | Y |

Comprehensive analysis of the 42 NB patient samples revealed that complete methylation (i.e., the absence of appreciable PCR product using the unmethylated DNA primer set) is most common in MYCN amplified neuroblastomas (Table 3). Ten of sixteen NB patient samples with MYCN amplification (63%), compared to only one of twenty-six samples without MYCN amplification (4%), contained completely methylated CASP8 alleles. Deletions of 2q33 were not frequently detected in either group of patient samples using the BAC clone containing both CASP8 and CASP10. Of possible interest, complete methylation, and therefore silencing, of CASP8 did not occur in six of six late stage (i.e., stage 4) neuroblastoma patient samples that did not contain amplified MYCN genes (Table 3; SJ-910007, SJ-970009, POG-687, POG-770, POG-1315, POG-3169, POG-5044). Furthermore, complete methylation of CASP8 occurred in one patient sample (i.e., POG-5217; Table 3) from a stage two neuroblastoma with MYCN amplification.

Thus, silencing of CASP8 by methylation appears to be almost exclusively associated with MYCN gene amplification in both the neuroblastoma patient samples and cell lines. This is the same sub-population of neuroblastoma patients known to have the poorest prognosis (Brodeur et al., Cancer, 1992, 70:1685–1694). Partial methylation of CASP8 takes place in early stages of neuroblastoma, which might suggest that its methylation precedes the amplification of the MYCN gene.

Example 4

The Use of Caspase-8 Overexpression to Determine the Functional Relevance of Caspase-8 Deficiency in Inhibition of Apoptosis and the Development of Cancer. The Use of Caspase-8 Overexpression as a Therapeutic Method to Sensitize Tumor Cells to Chemotherapeutic Drug Treatment Materials and Methods Expression constructs. The cell microinjection experiments employed a Fas receptor expression construct (Cheng et al., Science, 1994, 263:1759–1761), a DR3 expression construct (Kitson et al., Nature, 1996, 384:372–375), and an FADD and caspase-8(DN) expression constructs (Persons et al., Blood, 1999, 93:488–499; Yeh et al., Science, 1998, 279:1954–1958). Full-length wild type and dominant negative (DN) caspase-8 cDNAs were subcloned directly into pSP72 (Promega). Wild-type and DN caspase-8 cDNA inserts were then removed by Cla I and Sal I digestion from pSP72 and ligated into the Nsp V and Xho I sites of pMSCV-IGFP(M), respectively. Retrovirus supernatants were prepared as previously described (Persons et al., Blood, 1999, 93:488–499). To prevent the spontaneous activation of caspase-8 during transfection, 50 mM zVAD-fmk was added into the cell culture medium. $2 \times 10^6$ NB7, NB8 and NB10 cells were prepared the day before transduction in 10-mm culture dishes. 5 ml of the pMSCV-Casp8

(wt) and pMSCV-Casp8(DN) viral soups were quickly thawed at 37° C. and directly added to the cells and mixed gently with 5 ml of normal culture medium. 10 ml Polybrene (final concentration 4 mg/ml) was added into the culture medium and the cells incubated for 12–14 hrs at 37° C. After replacing this media with fresh viral soup and culture media, the cells were incubated at 37° C. for an additional 48 hrs. The transduced cells were sorted out by GFP expression using FACS, and the GFP-positive cells placed back into cell culture incubator for next experiment. Standard immunoblotting using the caspase-8 mAb (C15) was performed to demonstrate that caspase-8 was expressed in the viral transduced NB7, NB8 and NB10 cells and normal NB7, NB8 and NB10 cells.

Apoptotic assays. Cells were collected for annexin V-FITC staining and FACS analysis after the culture media containing zVAD-fmk was removed and replaced with normal culture medium for 6 hours in NB8 and NB 10. For NB7, anti-FAS antibody (100 ng/ml of CH-11) or TNFα (100 ng/ml) plus CHX (1 mg/ml) were then added to the cells and annexin-V-PE (PharMingen) staining performed as previously described (Tang et al., J. Biol. Chem., 1999, 274:7245–7252). Cell survival assays were performed by standard trypan blue exclusion assay and analysis of nuclear DNA condensation by DAPI staining (Janicke et al., Mol.Cell.Biol., 1994, 14:5661–5670). Viable cells were determined by light and immunofluorescent microscopy after removal of the zVAD-fmk containing culture medium and incubation at 37° C. for 0.5, 1, 2, 4 and 6 hrs for the pMSCV-Casp 8(wt) and DN transduced NB8 and NB10 cells.

Results

To use caspase-8 as a target for anti-cancer therapy, it is essential to determine whether the loss of caspase-8 expression in the neuroblastoma cell lines is functionally relevant. All studied NB cell lines express either the Fas or DR3 receptors (FIG. 5, Table 2, and Grenet et al., Genomics, 1998, 49:385–393), both of which signal through FADD-dependent recruitment of caspase-8 (Kitson et al., Nature, 1996, 384:372–375; Muzio et al., Cell, 1996, 85:817–827). In addition, even though all of the NB cell lines express caspase-10 (FIG. 4D), death receptor aggregation in response to Fas mAb or DR3 death receptor overexpression did not trigger cell death or result in caspase-10 processing (Table 4; data not shown).

Figure 8A:
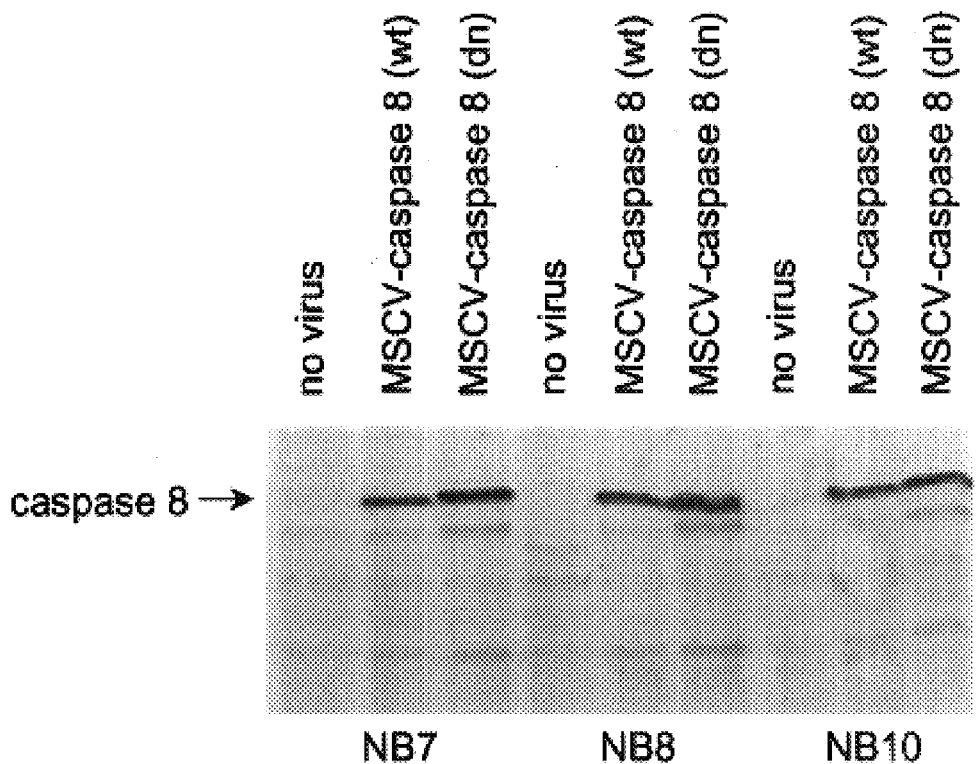
Figure 8B:
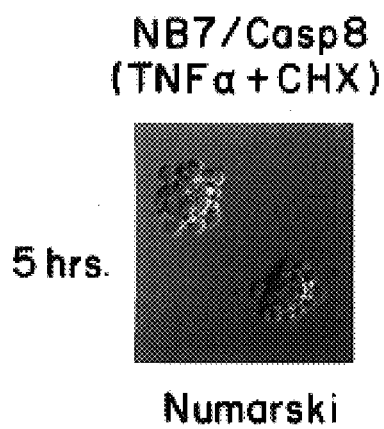
Figure 8C:
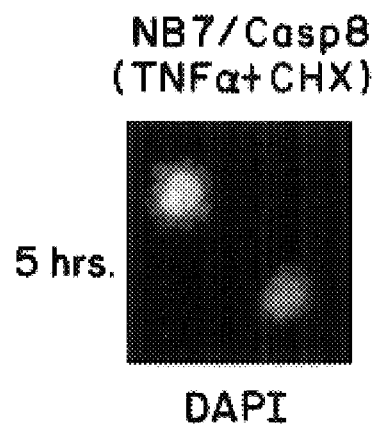
Figure 8E:
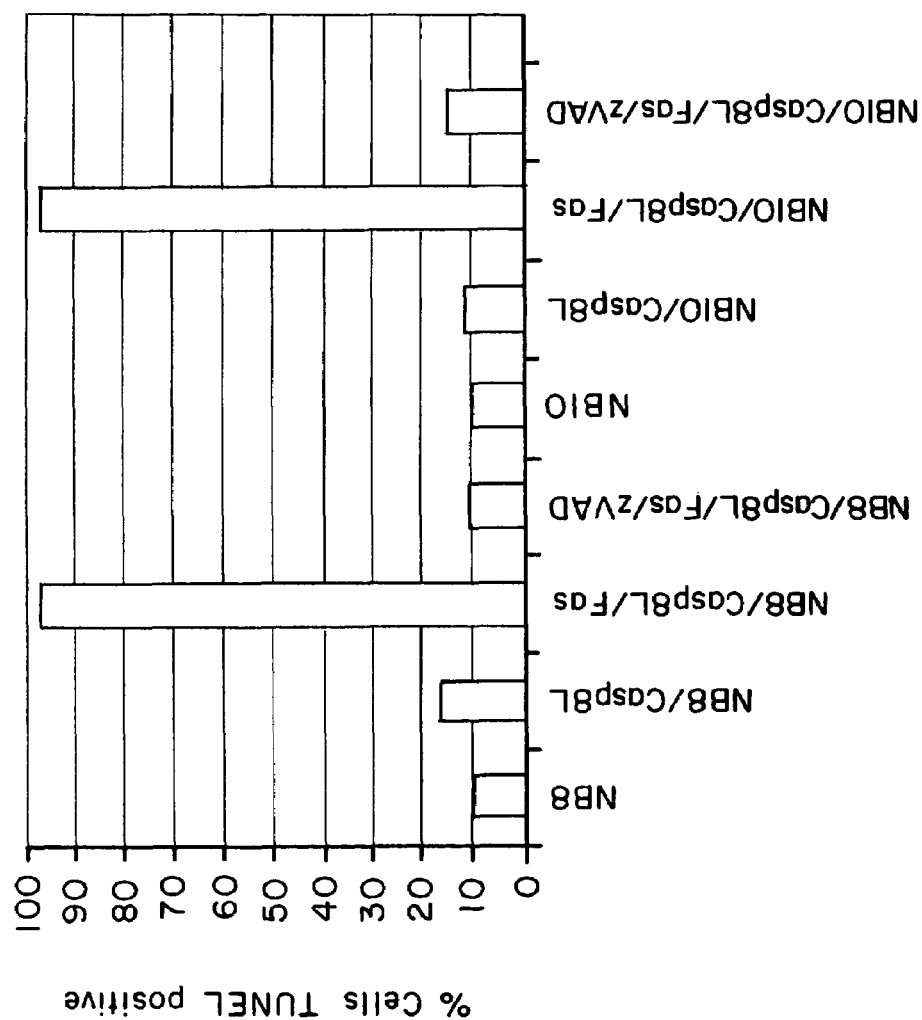

To further examine the possible functional relevance of the caspase-8 deficiency, both Fas positive (NB8, NB10) and Fas negative (NB7) cell lines were transduced with a retroviral vector containing either wild-type caspase-8 (pMSCV-Casp8(wt)) or an inactive form of caspase-8 (pMSCV-Casp8 (DN); Muzio et al., Cell, 1996, 85:817–827). Caspase-8 expression programmed by the vector was verified by immunoblot analysis (FIG. 8A). Since NB7, the cell line with homozygous CASP8 deletion, does not express Fas receptor, an alternative death receptor was chosen to induce apoptosis. TNFR p55, a Fas-related death receptor, is expressed in NB7 cells, and when these cells were treated with TNF-α and cycloheximide (CHX) it promotes apoptosis only if retrovirally programmed caspase-8 is expressed and active (Yeh et al., Science, 1998, 279: 1954–1958; Varfolomeev et al., Immunity, 1998, 9: 267–276). Five hours after TNF-α/CHX treatment, approximately 5% of the NB7 cells lacking caspase-8 were apoptotic (FIG. 8D), while approximately 40% of the pMSCV-Casp8(wt) cells had undergone apoptosis as judged by the condensed appearance of DAPI-stained nuclei (FIG. 8C) and annexin-V-FITC staining (FIG. 8D). Expression of high levels of wild-type caspase-8, but not caspase-8(DN), in NB8 and NB10 cells resulted in 60–65% cell death in the absence of apoptotic stimuli (FIG. 8D). When stable NB8 and NB10 cell populations expressing lower, non-lethal, levels of caspase-8 were selected, they did not undergo significant apoptosis in the absence of an appropriate stimulus (FIG. 8E). However, addition of agonistic Fas mAb to NB8 culture media resulted in greater than 98% cell death within six hours (FIG. 8E). If the potent caspase inhibitor zVAD-fmk (Milligan et al., Neuron, 1995, 15:385–393) was added to the cell culture media prior to programmed expression of caspase-8, apoptosis induced by agonistic Fas mAb was blocked in both cell lines no matter what the level of caspase-8 expression (FIGS. 8D and 8E).

Although the participation of caspase-8 in tumor cell death induced by chemotherapeutic drug treatment has been considered a controversial issue, it has been suggested that both Fas/CD95-dependent and independent activation of caspase-8 is involved (Landowski et al., Blood, 1999, 94:265–274; Fulda et al., Cancer Res., 1997, 57:3823–3829). In further support of this, we found that NB cell lines (e.g., NB16 and NB21) expressing caspase-8 are more sensitized to doxorubicin-induced apoptosis, whereas cell lines that do not express caspase-8 are not sensitized, regardless of their Fas/CD95 expression status (Table 4). In order to determine whether exogenous expression of caspase-8 resensitized caspase-8 null NB cells to chemo-

TABLE 4

Apoptotic function of selected human neuroblastoma cell lines +/− caspase-8

| Cell Line | DR3-induced Apoptosis[1] | FADD-induced Apoptosis[1] | DR3/FADD-induced Apoptosis[1] | Caspase-8 protein | FasR protein | Doxorubicin-induced Apoptosis[2] | Doxorubicin-induced Apoptosis (+caspase-8)[2] |
|---|---|---|---|---|---|---|---|
| NB3 | N/A | N/A | N/A | Y | Y | 52 +/− 4% | — |
| NB5 | N/A | N/A | N/A | Y | Y | 54 +/− 4.6% | — |
| NB7 | N | N | N | N | N | 24 +/− 3% | 42 +/− 2.6% |
| NB8 | N | N | N | N | Y | 18 +/− 2.6% | 38 +/− 2% |

[1]Apoptosis induced by overexpression of these proteins after microinjection of appropriate expression plasmids into NB7, NB8 and NB16. Apoptosis was assessed by TUNEL. N, less than 10% TUNEL-positive cells; Y, greater than 80% TUNEL-positive cells. Results represent three independent experiments.
[2]Apoptosis induced by treatment with 0.1 mM doxorubicin for 48 hrs, in three independent experiments, as described by others (Fulda et al., Cancer Res., 1997, 57: 3823–3829). Percentage of cell death was determined by TUNEL.

therapeutic agents, NB7 cells and NB7 cells transduced with pMSCV-Casp8(wt) were treated with doxorubicin. Doxorubicin-induced neuroblastoma apoptosis has previously been linked to the Fas receptor pathway (Fulda et al., Cancer Res., 1997, 57:3823–3829). The NB7 cell line was chosen since it lacks a functional CASP8 gene (FIGS. 4 and 5, Table 2). While the parental NB7 cells, as well as those transduced with pMSCV or pMSCV-Casp8(DN), underwent very limited apoptosis after exposure to low levels of doxorubicin, those expressing functional caspase-8 underwent a 70–100% increase in the level of cell death (Table 4). Thus, NB7 cells expressing functional caspase-8 are resensitized to treatment with doxorubicin, demonstrating that caspase-8 expression and activation are capable of accelerating NB7 cell apoptosis and that caspase-8 is functionally relevant to this form of cell death.

Discussion

These data suggest that inactivation of the Fas apoptotic pathway through epigenetic modification of caspase-8 expression contributes to the survival of many neuroblastoma cells that acquire high levels of Myc-N through gene amplification. Caspase-8 has been shown to play a pivotal role in apoptosis induced by activated death receptors (Askew et al., Oncogene, 1991, 6: 1915–1922; Kitson et al., Nature, 1996, 384: 372–375), chemotherapeutic drugs (e.g., doxorubicin) and irradiation (Friesen et al., Nature Med., 1996, 2: 574–577; Fulda et al., Cancer Res., 1997, 57: 3823–3829). In at least one NB cell line, loss of caspase-8 expression appears to contribute to reduced levels of doxorubicin-induced apoptosis, as well as the dysregulated proliferation, that characterize MYCN amplified neuroblastoma.

The results of the present studies further suggest that an analysis of CASP8 methylation status, particularly in tumors overexpressing myc oncoproteins, might prove to be a useful diagnostic tool. Caspase-8 gene transfer studies, the use of specific demethylating agents, and/or the use of specific methylase inhibitors may also need to be considered as potential treatments for neuroblastomas with MYCN amplification. Augmentation of chemotherapeutic/irradiation treatment regimens in this manner might enhance their effectiveness, thereby improving the prognosis for these patients.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, are approximate, and are provided for description.

Patents, patent applications, procedures, and publications cited throughout this application are incorporated herein by reference in their entireties.

What is claimed is:

1. A method for detecting inactivation of a CASP8 gene expression in a primary cancer cell, comprising detecting methylation of CASP8 genomic DNA.

2. The method according to claim 1, wherein the methylation occurs in the 5' untranslated region of CASP8 genomic DNA.

3. The method according to claim 2, wherein the methylation occurs in sequences selected from the group consisting of SEQ ID NO: 1 and SEQ ID NO: 2.

4. The method according to claim 1, wherein the methylation of CASP8 genomic DNA is detected by a methylation polymerase chain reaction (PCR) assay.

5. The method according to claim 4, wherein the PCR assay utilizes at least one of the primer sequences selected from the group consisting of SEQ ID NO: 29, SEQ ID NO: 30, SEQ ID NO: 31, SEQ ID NO: 32, SEQ ID NO: 33, and SEQ ID NO: 34.

6. A kit for detecting inactivation of a CASP8 gene expression, comprising oligonucleotide primer pairs for amplification of SEQ ID NO: 1 or SEQ ID NO: 2; wherein said primer pairs are oligonucleotides of at least 10 nucleotides that hybridize to SEQ ID NO: 1 or SEQ ID NO: 2 or to complete complements thereof, in a methylation polymerase chain reaction (PCR) assay for the detection of methylation of SEQ ID NO: 1 or SEQ ID NO: 2.

7. A kit of claim 6, wherein the kit comprises at least one primer pair, wherein at least one of the oligonucleotide primers is selected from the group consisting of SEQ ID NO: 29, SEQ ID NO: 30, SEQ ID NO: 31, SEQ ID NO: 32, SEQ ID NO: 33, and SEQ ID NO: 34.

8. A method for prognosis of a neuroblastoma comprising detecting inactivation of a CASP8 gene expression in a neuroblastoma cell from a subject, wherein said inactivation of a CASP8 gene expression in the neuroblastoma cell is indicative of the inefficiency of apoptosis induced by activated death receptors, chemotherapeutic drugs, or irradiation, and wherein said method comprises detecting a methylation of CASP8 genomic DNA.

9. The method according to claim 8, wherein the neuroblastoma is a tumor in which a myc gene is amplified.

10. The method according to claim 8, wherein the methylation of CASP8 genomic DNA is detected by methylation polymerase chain reaction (PCR) assay.

11. A method for diagnosis of an aggressive neuroblastoma comprising detecting inactivation of a CASP8 gene expression in a neuroblastoma cell from a subject, wherein said inactivation of a CASP8 gene expression in the neuroblastoma cell is indicative of the presence of an aggressive neuroblastoma and wherein said method comprises detecting a methylation of CASP8 genomic DNA.

12. The method according to claim 11, wherein the neuroblastoma is a tumor in which a myc gene is amplified.

13. The method according to claim 11, wherein the methylation of CASP8 genomic DNA is detected by methylation polymerase chain reaction (PCR) assay.

* * * * *

SEQUENCE LISTING

<160> NUMBER OF SEQ ID NOS: 34

<210> SEQ ID NO 1
<211> LENGTH: 670
<212> TYPE: DNA
<213> ORGANISM: Human

<400> SEQUENCE: 1

```
aagcgctcca agacacgatt gcagaaggaa cacggggtgg ccaactgaaa tttgaagaac      60
agggccaagg atgggaactc agcctgagca cgggttgatc cggagcaggg ctaagccaag     120
tacgaatgaa ccagaccact tcctcctttt tttctgaacg atctacccgc atttcagcca     180
cagggctgac tttacccagt ccggcgggag ggaggagagg gctggtctgt gacttcagtg     240
ctgaggtttg atcaaggcaa agggaaactt cctattccca gacccttgc aagaaagaat      300 ggcatattac ttgccgccga caggggttat tattactaaa tggagtcagt ataaatgctt     360
tccaataaag catgtccagc gctcgggctt tagtttgcac gtccatgaat tgtctgccac     420
atccctcttc tgaatggttg gaattgggca tctctgttcc tttaaacagg aaacatttct     480
tgttcgagtg agtcatctct gttctgcttt aggagtaaag tttaccctgc agttccttct     540
gtggtgaagt tttctctttc tctcggagac cagattctgc ctttacgctg gagggaagtg     600
ttttcacagg ttctcctcct tttatctttt gtgttttttt tcgagccatg ggggttaaat     660
aaagcgcttt                                                            670
```

<210> SEQ ID NO 2
<211> LENGTH: 753
<212> TYPE: DNA
<213> ORGANISM: Human

<400> SEQUENCE: 2

```
aattagaccg cgtattgaaa gtaaaagaaa cttcttcctg ggagcctttc ccacccctt      60
ccctgctgag cacgtggagt taggcaggtt aggggactcg gagactgcga tggtgccagg    120
aaagggtgga gcgggtgagt gcctgttgcc aaggtggcct cttcaacagg aaaccacaat    180
attttttgttt cttgacttgc tctagaaaca gggctgtggg ggtgggaag caacttggat    240
ctgccttct gaggacacct ctggtgctgc ctggcccagg tctcctgtgt ggtttctctc     300
tgagccgatg cctttgactt tgctacttttt tcactctgag cagtctccag ttcctctgct   360
accttttttgt cctccaagct tccctgccgc ctcgaatgca gatacacgga ctcccttctg   420
tggacccgtt tggagagtcc agaagacttt atcaatccac ttttttttct ttttcatttg   480
gccctggggg ccgacggtta agtactttat tctgtcattc tgtcgaatca cgaatgccct   540
gaggtgcaca gccccttttcc cctctttcgc gtcctgaagg ggtttccttt tatgtcttcc   600
accccaccc tttcccctcc ctgccctctg tttttgttgc ccaaaaaaca agttctctaa    660
acgttttcga tgtggattcg cggaaaatta acctgcaccc gtttgcaaaa tgaactttt    720
tttttttgatc ctgtacactg gttttttaac ctt                                753
```

<210> SEQ ID NO 3
<211> LENGTH: 879
<212> TYPE: DNA
<213> ORGANISM: Human

<400> SEQUENCE: 3

```
ccaccgcgcc cagcccattg gcttgtttgt atgtctacct tcctaaacag taagagggaa     60
cttgtctggt gttctttttt tctctcctgt gctgacagca caatgaccag tacctagtag    120
ttgcagtagc ctttgatgaa caagccagca aatggtactt tcttcctta tctgaacata     180
ccatttattt tgacttagat tatattctcc tgccttttaa aaagatggac ttcagcagaa    240
atctttatga tattggggaa caactggaca gtgaagatct ggcctccctc aagttcctga   300
gcctgaacta cattccgcaa aggaagcaag aacccatcaa ggatgccttg atgttattcc   360
agagacycca ggaaaagaga atgttggagg aaagcaatct gtccttcctg aaggagctgc   420
tcttccgaat taatagactg gatttgctga ttacctacct aaaacactaga aaggaggaga  480
tggaaaggga acttcagaca ccaggcaggg ctcaaatttc tgcctacagg tgggtggaaa   540
ctcccattgt gggactggga ggtgtgggtt gaatggacag cctctgagct gattgggct    600
ttttttttgtg gtaccctgcc tagtgcctgg gaacccagca gtgccacaat tctaaagctt   660
ctacagaaga cagtagtgcc ttggtggtcc tgctaaaggc tgtaaaactt agcttctccc   720
caccctagag agagtgggta aacaaaggcg tgagagagaa accaacattc agtatcactt    780
gggaggcttt gggaagatgt cccaccggag ccagattaag aaatttaggg gccttatata   840
taattctata gaaatgctaa gaccataaaa taaaaattt                           879
```

<210> SEQ ID NO 4
<211> LENGTH: 659
<212> TYPE: DNA
<213> ORGANISM: Human

<400> SEQUENCE: 4

```
ccgcgcgttg gccgattcat taatgcagct ggcacgcagg tttcccgact ggaaaagcgg     60
gcagtgagcg caacgcaatt aatgtgagtt agtcactctt aggcactcca tggcccatgc    120
```

-continued

```
cattactggc tttatgttga gggtggcctt tgggatccga gccccctgtg gctccatata      180
tcacatggga cttatttggc caagatttct aaagtgtctc catttcccaa ccacaaaggg      240
tcatgctcta tcagatttca gaagaagtga gcagatcaga attgaggtct tttaagtttc      300
ttttgcaaga ggaaatctcc aaatgcaaac tggatgatga catggtgcct gggaacagca      360
ggccacaatt ctaagcttct acagaaaaga cagtagtgcc ttgggtggcc tgctaaaggc      420
tgtaaaactt agcttctccc caccctagag agagtgggta acaaaggcg tgagagagaa       480 accacattca gtatcacttg ggaggctttg ggaagatgtc ccaccggagc cagattaaga      540
aatttagggg cctatatat aattctatag aaatgctaag accataaaat aaaaatttat       600
ttttcaaagt gaaacattac ttagaggtat gctgaagtta aatagagtt tttctaagt        659
```

<210> SEQ ID NO 5
<211> LENGTH: 448
<212> TYPE: DNA
<213> ORGANISM: Human

<400> SEQUENCE: 5

```
ggggactggg tgacatctga catggcttct cctttatcct ctcacttctg tctttctggg      60
ccagaaaaca tggaatcgct tccctagtag cctgctggct gtgagagacc agcagaaact      120
gtcagaaact tgggaagcaa gggcaggtcc ttggttggag aaattggaaa ttaaaaaaaa      180
aaatctaatc taaaaaccag tagggctcaa tcagattcca actttatttc tcctcctctt      240
acaacctgct ggatattttc atagagatgg agaagagggt catcctggga gaaggaaagt      300
tggacatcct gaaagagtc tgtgcccaaa tcaacaagag cctgctgaag ataatcaacg       360
actatgaaga attcagcaaa gtaccgcaat tccctatgtt ttaacgcagc ataggtcaga      420
agggggcctg cgcagctcga taatctgg                                         448
```

<210> SEQ ID NO 6
<211> LENGTH: 228
<212> TYPE: DNA
<213> ORGANISM: Human

<400> SEQUENCE: 6

```
cccgcctcta ctaagttttg atagctggca aaatcggcta ccatatcaca ggtgttttta      60
gtcaactgtt gttcgggggt acccttgcc ttatctgagg agagaagcag cagccttgaa       120
ggaagtcctg atgaattttc aaatgttagt taatttacta tctggtacct gcatgtgttc      180
tcccttcagc cttctaccac atgcacatct taacgtgcct gctctact                   228
```

<210> SEQ ID NO 7
<211> LENGTH: 177
<212> TYPE: DNA
<213> ORGANISM: Human

<400> SEQUENCE: 7

```
cgggtcaccc ttggggtaaa ttttcccggg ttttcccgag ggggaggagt tgtgtggggt      60
aatgacaatc tcggactctc caagagaaca ggatagtgaa tcccaggtag cacggaaaac      120
ctccaaatcc tttttttac attacattac agattctagt ttttaattt gttagct           177
```

<210> SEQ ID NO 8
<211> LENGTH: 784
<212> TYPE: DNA
<213> ORGANISM: Human

<400> SEQUENCE: 8

```
aatattaata tatgtgcaaa gtgctcagga ggcccaggta ttgggacact gactttacaa      60
cgatggggca gaagtctgag aggtcctgtg tgaaggaaat aggtagaaac tagttcttcg     120
aggaaacgac cccgagttgg ggtggtgcaa tggaaagcaa gtcctcttac tagggagttg     180
tttgtttaca tctctagtgt tgacccacag agtcagctcc tgggttgggt tttttgtaat     240
ccagactttg acaaagttt accaaatgaa agcaaacct cggggatact gtctgatcat       300
ccaacaatca caattttgca aaagcacggg agaaagtgcc caaacttcac agcattaggg     360
acaggaatgg aacacacttg gatgcaggtg ggcgggctc gtgagcgtgc cttccaaatt      420
cccccaaatg ggagaaaatc cttcttatgc ctattttttt ttaaatcaaa agggatttaa     480
catagctata ccaaaaggc catggttcaa gaaaatggat ttaaacatat ttccctgtgg      540
aggtaaagaa cattcttata catttatcag tttcctgctt tttttaaaaa ttaatttttt     600
aaataaaagt aatgtatgta taaatataaa atatcaaatc ttactaaaag acataatgaa     660
aagcagtaat aagctttgtt ttgaattcag ctaaatgcat agcgcttctg tggaatgtat     720
taggcgatga aaatgctggt gggatcaaag ccttatagag ctgcattttt tacaggttgg     780
gctg                                                                  784

<210> SEQ ID NO 9
<211> LENGTH: 771
<212> TYPE: DNA
<213> ORGANISM: Human

<400> SEQUENCE: 9
ggtcctttgc ttgtctctcg gtgtcctgca ctctccctct cctgctggtc tgtgcttgct      60
atagtgtggc gtactgttcg agtttcactt ttcaggggct tgaccacga ctttgaagag     120 cttcattttg agatcaagcc ccacgatgac tgcacagtag agcaaatcta tgacattttg     180
aaaatctacc aactcatgga ccacagtaac atggactgct tcatctgctg tatcctctcc     240
catggagaca agggcatcat ctatggcact gatggacagg agcccccat ctatgagctg      300 acatctcagt tcactggttt gaagtgccct tcccttgctg gaaaacccaa agtgtttttt     360
attcaggatt gtcaggggga taactaccag aaaggtatac ctgttgagac tgattcagag     420 gagcaacccct atttagaaat ggatttatca tcacctcaaa cgagatatat cccggatgag     480
gctgactttc tgctggggat ggccactgtg aataactgtg ttcctaccga aaccctgcag     540
agggaacctg gtacatccag tcactttgcc agagcctgag agagcgatgt cctcggtaag    600
ttttgcctac tcagccctcc tcactgttac actaccttcc ccccctactc catcacacta    660
ctatctactc atattcagag cctattgaaa agtgctatgt gatttagatc acattaacag    720
gtcagagaac tgtccaaggg gagtggttc cgttcaactc taaatgtcta g              771

<210> SEQ ID NO 10
<211> LENGTH: 223
<212> TYPE: DNA
<213> ORGANISM: Human

<400> SEQUENCE: 10
cttcgtggtc tgtctctggg cccgcaggcc cccagttctc cgtgctttcc ccctcagccg      60
tcgcaatagt gtgtgaatag tttgcagagg cgatgatatt ctcaccatcc tgactgaagt     120
gaactatgaa gtaagcaaca aggatgacaa gaaaaacatg gggaaacaga tgcctcagcc    180
tactttcaca ctaagaaaaa aacttgtctt cccttctgat tga                      223
```

```
<210> SEQ ID NO 11
<211> LENGTH: 5
<212> TYPE: PRT
<213> ORGANISM: Human
<220> FEATURE:
<223> OTHER INFORMATION: Xaa at position four is any amino acid.

<400> SEQUENCE: 11

Gln Ala Cys Xaa Gly
 1               5

<210> SEQ ID NO 12
<211> LENGTH: 8
<212> TYPE: PRT
<213> ORGANISM: Human

<400> SEQUENCE: 12

Arg Asn Pro Ala Glu Gly Thr Trp
 1               5

<210> SEQ ID NO 13
<211> LENGTH: 20
<212> TYPE: DNA
<213> ORGANISM: Human

<400> SEQUENCE: 13
ggtggagcgg gtgtgggtcg                                              20

<210> SEQ ID NO 14
<211> LENGTH: 23
<212> TYPE: DNA
<213> ORGANISM: Human

<400> SEQUENCE: 14
tattttgact tagattatat tct                                          23

<210> SEQ ID NO 15
<211> LENGTH: 22
<212> TYPE: DNA
<213> ORGANISM: Human

<400> SEQUENCE: 15
gcctacaggt gggtggaaac tc                                           22

<210> SEQ ID NO 16
<211> LENGTH: 20
<212> TYPE: DNA
<213> ORGANISM: Human

<400> SEQUENCE: 16
cccaaccaca aagggtcatg                                              20

<210> SEQ ID NO 17
<211> LENGTH: 21
<212> TYPE: DNA
<213> ORGANISM: Human

<400> SEQUENCE: 17
gatgacatgg tgcctgggaa c                                            21

<210> SEQ ID NO 18
<211> LENGTH: 21
<212> TYPE: DNA
<213> ORGANISM: Human
```

```
<400> SEQUENCE: 18
ttctcctcct cttacaacct g                                              21

<210> SEQ ID NO 19
<211> LENGTH: 22
<212> TYPE: DNA
<213> ORGANISM: Human

<400> SEQUENCE: 19
ttcagcaaag taccgcaatt tc                                             22

<210> SEQ ID NO 20
<211> LENGTH: 21
<212> TYPE: DNA
<213> ORGANISM: Human

<400> SEQUENCE: 20
tttgccttat ctgaggagag a                                              21

<210> SEQ ID NO 21
<211> LENGTH: 23
<212> TYPE: DNA
<213> ORGANISM: Human

<400> SEQUENCE: 21
tcaaatgtta gttaatttac tat                                            23

<210> SEQ ID NO 22
<211> LENGTH: 23
<212> TYPE: DNA
<213> ORGANISM: Human

<400> SEQUENCE: 22
tcccgggttt tcccgagggg gag                                            23

<210> SEQ ID NO 23
<211> LENGTH: 21
<212> TYPE: DNA
<213> ORGANISM: Human

<400> SEQUENCE: 23
tcacaggtag cacggaaaac c                                              21

<210> SEQ ID NO 24
<211> LENGTH: 22
<212> TYPE: DNA
<213> ORGANISM: Human

<400> SEQUENCE: 24
gggttttgta atccagactt tg                                             22

<210> SEQ ID NO 25
<211> LENGTH: 20
<212> TYPE: DNA
<213> ORGANISM: Human

<400> SEQUENCE: 25
gatgcaggtg ggcggggctc                                                20

<210> SEQ ID NO 26
<211> LENGTH: 23
<212> TYPE: DNA
```

```
<213> ORGANISM: Human

<400> SEQUENCE: 26
agtttcactt ttcagggtct ttg                                           23

<210> SEQ ID NO 27
<211> LENGTH: 24
<212> TYPE: DNA
<213> ORGANISM: Human

<400> SEQUENCE: 27
tgtcctcggt aagttttgcc tact                                          24

<210> SEQ ID NO 28
<211> LENGTH: 22
<212> TYPE: DNA
<213> ORGANISM: Human

<400> SEQUENCE: 28
gtgaatagtt tgcagaggcg at                                            22

<210> SEQ ID NO 29
<211> LENGTH: 21
<212> TYPE: DNA
<213> ORGANISM: Human

<400> SEQUENCE: 29 tagggattc ggagattgcg a                                              21

<210> SEQ ID NO 30
<211> LENGTH: 22
<212> TYPE: DNA
<213> ORGANISM: Human

<400> SEQUENCE: 30
cgtatatcta cattcgaaac ga                                            22

<210> SEQ ID NO 31
<211> LENGTH: 21
<212> TYPE: DNA
<213> ORGANISM: Human

<400> SEQUENCE: 31 tagggattt ggagattgtg a                                              21

<210> SEQ ID NO 32
<211> LENGTH: 25
<212> TYPE: DNA
<213> ORGANISM: Human

<400> SEQUENCE: 32
ccatatatat ctacattcaa aacaa                                         25

<210> SEQ ID NO 33
<211> LENGTH: 21
<212> TYPE: DNA
<213> ORGANISM: Human

<400> SEQUENCE: 33 tagggactc ggagactgcg a                                              21

<210> SEQ ID NO 34
<211> LENGTH: 21
```

```
<212> TYPE: DNA
<213> ORGANISM: Human

<400> SEQUENCE: 34
cgtgtatctg cattcgaggc g                                        21
```